(12) United States Patent
Murray et al.

(10) Patent No.: US 12,431,239 B1
(45) Date of Patent: *Sep. 30, 2025

(54) UTILIZING PREDICTIVE MODELING TO IDENTIFY ANOMALY EVENTS

(71) Applicant: C/HCA, Inc., Nashville, TN (US)

(72) Inventors: Scott Murray, Lemmesaw, GA (US); Dan Nguyen, Tampa, FL (US); Janet McCallister, Tallahassee, FL (US); Tara Haines, Tallahassee, FL (US); Erica Williams, Cairo, GA (US); George Tucker, Orange Park, FL (US); Heather Fuller, Tallahassee, FL (US); Randy Scott Fagin, Nashville, TN (US); Thomas Neal Payne, Austin, TX (US); Sarah Dhane, Austin, TX (US); James E. Hicks, Spring Hill, TN (US); Christopher Anthony, Franklin, TN (US); Chigger Bynum, Nashville, TN (US); Brooke Hamilton, Nashville, TN (US); Hannah Marshall, Asheville, NC (US); Megan McGee, Nashville, TN (US); Edmund Jackson, Nashville, TN (US)

(73) Assignee: C/HCA, Inc., Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/930,928

(22) Filed: Oct. 29, 2024

Related U.S. Application Data

(63) Continuation of application No. 17/683,496, filed on Mar. 1, 2022, now Pat. No. 12,131,819, which is a
(Continued)

(51) Int. Cl.
*G06F 16/00* (2019.01)
*G16H 10/60* (2018.01)
(Continued)

(52) U.S. Cl.
CPC ............. *G16H 40/20* (2018.01); *G16H 10/60* (2018.01); *G16H 15/00* (2018.01)

(58) Field of Classification Search
None
See application file for complete search history.

(56) References Cited

U.S. PATENT DOCUMENTS 5,991,728 A 11/1999 DeBusk et al.
7,661,127 B2 * 2/2010 Hirsch .................. H04L 63/105
726/28
(Continued)

OTHER PUBLICATIONS

Non-Final Office Action mailed on Aug. 21, 2019 in related U.S. Appl. No. 15/652,494, 15 pages.

*Primary Examiner* — Hasanul Mobin
(74) *Attorney, Agent, or Firm* — Kory D. Christensen

(57) ABSTRACT

Approaches are provided for a prediction model determining a prediction indicative of the authorized user being associated with at least one anomaly event. In one example, a computer system may receive data from different sources. For example, the system may receive data associated with use of one or more monitored units of an automated storage and retrieval location. The system may also receive request data associated with a request for execution of the monitored controlled unit by an authorized user to a target user. The prediction model of the system may utilize the received data to determine the prediction that the authorized user is associated with at least one anomaly event associated with a diversion of a monitored unit away from the target user. The system may then provide the prediction for presentation.

20 Claims, 16 Drawing Sheets

Related U.S. Application Data continuation-in-part of application No. 16/564,767, filed on Sep. 9, 2019, now Pat. No. 11,309,069, which is a continuation-in-part of application No. 15/652,494, filed on Jul. 18, 2017, now abandoned.

(60) Provisional application No. 63/157,555, filed on Mar. 5, 2021, provisional application No. 62/729,242, filed on Sep. 10, 2018, provisional application No. 62/363,615, filed on Jul. 18, 2016.

(51) Int. Cl.
*G16H 15/00* (2018.01)
*G16H 40/20* (2018.01)

(56) References Cited

U.S. PATENT DOCUMENTS

| | | | |
|---|---|---|---|
| 8,838,215 | B2 | 9/2014 | John et al. |
| 8,868,616 | B1 | 10/2014 | Otto et al. |
| 9,811,438 | B1* | 11/2017 | Barrett ............... G06F 11/3419 |
| 11,140,240 | B1* | 10/2021 | Brown ................... G06F 9/547 |
| 11,907,658 | B2* | 2/2024 | Chen ................... G06F 18/2415 |
| 2003/0083903 | A1 | 5/2003 | Myers |
| 2003/0149893 | A1* | 8/2003 | Chang ................... H04L 63/168 |
| | | | 726/28 |
| 2005/0020903 | A1 | 1/2005 | Krishnan et al. |
| 2009/0204436 | A1 | 8/2009 | Thorne et al. |
| 2009/0299766 | A1 | 12/2009 | Friedlander et al. |
| 2010/0235896 | A1* | 9/2010 | Hirsch ............... H04L 63/0823 |
| | | | 707/769 |
| 2011/0185422 | A1* | 7/2011 | Khayam ............. H04L 63/1425 |
| | | | 726/23 |
| 2013/0297348 | A1 | 11/2013 | Cardoza et al. |
| 2014/0358833 | A1* | 12/2014 | Biem ................... G06F 11/079 |
| | | | 706/21 |
| 2015/0106125 | A1 | 4/2015 | Farooq et al. |
| 2015/0244687 | A1 | 8/2015 | Perez et al. |
| 2015/0269433 | A1 | 9/2015 | Amtrup et al. |
| 2016/0027278 | A1 | 1/2016 | McIntosh et al. |
| 2016/0098542 | A1 | 4/2016 | Costantini et al. |
| 2016/0246941 | A1 | 8/2016 | Miller et al. |
| 2017/0323064 | A1 | 11/2017 | Bates |
| 2019/0020468 | A1* | 1/2019 | Rosenoer ............. H04L 9/3228 |
| 2019/0294485 | A1* | 9/2019 | Kukreja ............. G06F 11/0772 |
| 2020/0075150 | A1 | 3/2020 | Murray et al. |
| 2022/0109731 | A1* | 4/2022 | Morrison ............ H04L 67/141 |
| 2022/0358289 | A1* | 11/2022 | Chen ................... G06F 18/2415 |
| 2023/0244754 | A1* | 8/2023 | Schell ................. G06F 18/256 |
| | | | 706/12 |
| 2024/0020400 | A1* | 1/2024 | Chen ................... G06F 21/6227 |

* cited by examiner

UTILIZING PREDICTIVE MODELING TO IDENTIFY ANOMALY EVENTS

CROSS REFERENCE TO RELATED APPLICATIONS

This application is a continuation of U.S. patent application Ser. No. 17/683,496, filed Mar. 1, 2022, which claims the benefit of and priority to U.S. Provisional Application No. 63/157,555, filed Mar. 5, 2021. U.S. patent application Ser. No. 17/683,496 is also a continuation-in-part of U.S. application Ser. No. 16/564,767, filed Sep. 9, 2019, which claims the benefit of and priority to U.S. Provisional Application No. 62/729,242, filed Sep. 10, 2018. U.S. application Ser. No. 16/564,767 is also a continuation-in-part of U.S. application Ser. No. 15/652,494, filed Jul. 18, 2017, now abandoned, which claims the benefit of and priority to U.S. Provisional Application No. 62/363,615, filed Jul. 18, 2016. These applications are hereby incorporated by reference in their entirety for all purposes.

BACKGROUND

The amount of data generated each day continues to grow. In some environments, some of this data may be stored, while a majority of it may be evaluated and abandoned or ignored. Users and computing devices are beginning to rely more and on this data to make decisions. This may be especially true when the data is introduced as part of an operational flow. However, the time required to sort through stored data can create inefficiencies and the fact that other data may typically be ignored or abandoned may create undesirable outcomes.

SUMMARY

This specification relates in general to aggregating data from disparate data sources in a network environment and, but not by way of limitation, to aggregating the data and using the data for predictively identifying anomaly events. The data may also be used by a prediction model to determine a prediction score that a user is associated with one or more anomaly events.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a computer-implemented method. The computer-implemented method also includes receiving, by a computer system from a first data source, first data may include a plurality of first data attributes associated with a monitored controlled unit of an automated storage and retrieval location, the automated storage and retrieval location may include a lockable cabinet in which is stored monitored controlled units, and the first data associated with a type of use involving the monitored controlled unit. The method also includes receiving, by the computer system from a second data source, second data may include a plurality of second data attributes corresponding to a request for the monitored controlled unit of the monitored controlled units stored in the automated storage and retrieval location, the order associated with an electronic record of a dependent user, and the second data associated with an administration of the monitored controlled unit to the dependent user. The method also includes receiving, by the computer system from a third data source, third data may include a plurality of third data attributes associated with an authorized user of a facility that includes the automated storage and retrieval location. The method also includes determining, by a prediction model of the computer system, a prediction indicative of the authorized user being associated with at least one anomaly event the prediction determined based at least in part on at least one of the first data, the second data, or the third data, and where the prediction model is trained based at least in part on features derived from at least one of the first data attributes, the second data attributes, or the third data attributes. The method also includes providing, by the computer system, the prediction to a user device for presentation. Other embodiments of this aspect include corresponding computer systems, apparatus, and computer programs recorded on one or more computer storage devices, each configured to perform the actions of the methods.

Other objects, advantages, and novel features of the present disclosure will become apparent from the following detailed description of the disclosure when considered in conjunction with the accompanying drawings.

BRIEF DESCRIPTION OF THE DRAWINGS

Various examples in accordance with the present disclosure will be described with reference to the drawings, in which.

DETAILED DESCRIPTION OF THE INVENTION

The ensuing description provides preferred exemplary example(s) only, and is not intended to limit the scope, applicability or configuration of the disclosure. Rather, the ensuing description of the preferred exemplary example(s) will provide those skilled in the art with an enabling description for implementing a preferred exemplary example. It is understood that various changes may be made in the function and arrangement of elements without departing from the spirit and scope as set forth in the appended claims.

Figure 1:
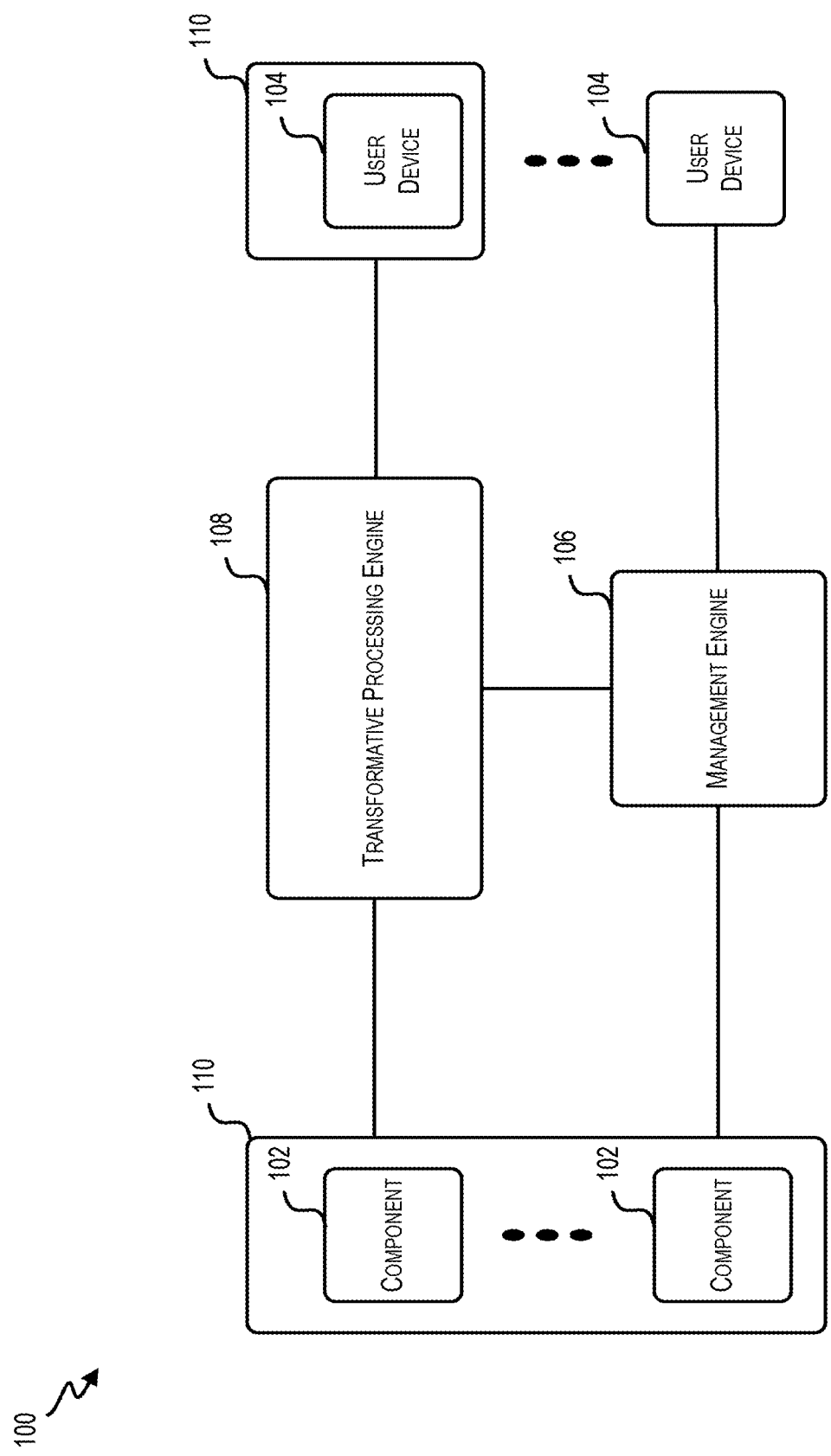
FIG. 1 is an example block diagram illustrating an interaction system in which techniques relating to aggregating data from disparate sources for anomaly event prediction may be implemented, according to at least one example.

Referring first to FIG. 1, a block diagram of an example of an interaction system 100 is illustrated. Generally, in interaction system 100, data can be generated at one or more system components 102 and/or user devices 104. Management engine 106 can manage the flow of communications within interaction system. Transformative processing engine 108 can receive, intercept, track, integrate, process, and/or store such data.

Data flowing in interaction system 100 can include a set of communications. Each of one, some of all communications can include (for example) an encoding type, authentication credential, indication of a content size, identifier of a source device, identifier of a destination device, identifier pertaining to content in the communication (e.g., an identifier of an entity), a processing or reporting instruction, a procedure specification, transmission time stamp, and/or sensor measurement. Data may, or may not, selectively pertain to a particular entity and/or client. Data can, depending on the implementation, include individually identifiable information and/or de-identified information as it pertains to an entity and/or client. Data may, but need not, include protected information.

For example, a system component 102 can include, for example, a sensor to detect a sensor measurement and can thereafter generate and transmit a communication that reflects the sensor measurement. The communication may be transmitted at routine times and/or upon detecting a threshold (e.g., one or more) number of measurements or a measurement satisfying a transmission condition (e.g., exceeding a threshold value). In some instances, the sensor measurement corresponds to one reflecting a property of an object or entity (e.g., person) near the sensor. The communication may then include an identifier of the object or entity. The identifier can be determined, for example, based on detection of a nearby electronic tag (e.g., RFID tag), a detected user input received at a user interface of component 102, and/or data in a corresponding communication received from a user device.

As another example, a user device 104 can be configured to detect input received at an interface of the device. The input can include, for example, an identifier of an object or entity, an instruction, a characterization of an object or entity, an identification of an assessment to be performed, a specification of an aggregation or data processing to be performed, and/or an identification of a destination for a data-analysis report. User device 104 can further be configured to detect input requesting particular data, to generate a request communication (e.g., to be sent to transformative processing engine), to receive the requested data and/or to present the received data.

The depicted engines, devices and/or components can communicate over one or more networks. A network of one or more networks can include a wired network (e.g., fiber, Ethernet, powerline ethernet, ethernet over coaxial cable, digital signal line (DSL), or the like), wireless network (e.g., Zigbee™, Bluetooth™, WiFi™, IR, UWB, WiFi-Direct, BLE, cellular, Long-Term Evolution (LTE), WiMax™, or the like), local area network, the Internet and/or a combination thereof. It will be appreciated that, while one or more components 102 and one or more user devices 104 are illustrated as communicating via transformative processing engine 108 and/or management engine 106, this specification is not so limited. For example, each of one or more components 102 may communicate with each of one or more user devices 104 directly via other or the same communication networks.

A component 102 can be configured to detect, process and/or receive data, such as environmental data, geophysical data, biometric data, chemical data (e.g., chemical composition or concentration analysis data), and/or network data. The data can be based on data detected, for example, via a sensor, received signal or user input. A user device 104 can include a device configured to receive data from a user and/or present data to a user. It will be appreciated that, in some instances, a component 102 is also a user device 104 and vice-versa. For example, a single device can be configured to detect sensor measurements, receive user input and present output.

A component 102 can be configured to generate a communication that is in one or more formats, some of which can be proprietary. For example, an imaging machine (e.g., one of one or more components 102) manufactured by company A, located within a first facility (e.g., facility 110), and belonging to a first client, may save and transfer data in a first format. An imaging machine (e.g., one of one or more components 102) manufactured by company B, located within the first facility (e.g., facility 110), and belonging to the first client, may save and transfer data in a second format. In some examples, data from certain components is transformed, translated, or otherwise adjusted to be recognizable by transformative processing engine 108. Thus, continuing with the example from above, when the imaging machines manufactured by companies A and B are located within the first facility belonging to the first client, they may nevertheless save and transfer data in different formats. In some examples, one or more components 102 communicate using a defined format.

In some examples, each of one or more components 102 are each associated with one or more clients within a same or different interaction systems. For example, certain ones of one or more components 102 may be associated with a first client, while other ones of one or more components 102 may be associated with a second client. Additionally, each of one or more components 102 may be associated with a facility 110 (e.g., client facility). Each facility 110 may correspond to a single location and/or focus. Exemplary types of facilities include server farm facilities, web-server facilities, data-storage facilities, telecommunication facilities, service facilities, and/or operational facilities. For example, a first facility may include a structure at a first location at which one or more resources (e.g., computational resources, equipment resources, laboratory resources, and/or human resources) are provided. Each of the one or more resources may be of a first type in a first set of types. A resource type can be identified based on, for example, a characteristic of the resource (e.g., sensor inclusion) and/or a capability of providing each of one or more services. Thus, for example, resources at a first facility may be better configured for handling a particular type of service requests compared to those in another facility. As another example, different facilities may include resources of similar or same types but may vary in terms of, for example, accessibility, location, etc.

Transmission of data from one or more components 102 to transformative processing engine 108 may be triggered by a variety of different events. For example, the data may be transmitted periodically, upon detection of an event (e.g., completion of an analysis or end of a procedure), upon detection of an event defined by a rule (e.g., a user-defined rule), upon receiving user input triggering the transmission, or upon receiving a data request from transformative processing engine 108. Each transmission can include, e.g., a single record pertaining to a single entity, object, procedure, or analysis or multiple records pertaining to multiple entities, objects, procedures, or analyses.

In some examples, at least some of one or more user devices 104 are associated with facility 110. In some examples, at least some of one or more user devices 104 need not be associated with facility 110 or any other facility. Similar to one or more components 102, one or more user devices 104 may be capable of receiving, generating, processing, and/or transmitting data. Examples of one or more user devices 104 include, for example, a computer, a mobile device, a smart phone, a laptop, an electronic badge, a set-top box, a thin client device, a tablet, a pager, and other similar user devices). One or more user devices 104 may be configured to run one or more applications developed for interacting with data collected by transformative processing engine 108. For example, those user devices of one or more user devices 104 that are not associated with facility 110 may be configured to run one or more third-party applications that may rely in part on the data gathered by transformative processing engine 108.

Each of one or more components 102 and one or more user devices 104 may be utilized by one or more users (not shown). Each of the one or more users may be associated with one or more clients. For example, one of the one or more users can be associated with a client as a result of being employed by the client, physically located at a location of the client, being an agent of the client, or receiving a service from the client.

In some examples, one or more components 102 and one or more user devices 104 may communicate with transformative processing engine 108 and management engine 106 via different information formats, different proprietary protocols, different encryption techniques, different languages, different machine languages, and the like. As will be discussed with reference to FIG. 2, transformative processing engine 108 is configured to receive these many different communications from one or more components 102, and in some examples from one or more user devices 104, in their native formats and transform them into any of one or more formats. The received and/or transformed communications can be transmitted to one or more other devices (e.g., management engine 106, an entity device, and/or a user device) and/or locally or remotely stored. In some examples, transformative processing engine 108 receives data in a particular format (e.g., the HL7 format) or conforming to any other suitable format and/or is configured to transform received data to conform to the particular format.

One or more components 102 of facility 110 can include and/or has access to a local or remote memory for storing generated data. In some examples, the data is stored by one or more servers local to facility 110. The record service can be granted access to the data generated and/or transmitted by one or more components 102. In some examples, the record service includes a server or a plurality of servers arranged in a cluster or the like. These server(s) of the record service can process and/or store data generated by one or more components 102. For example, one or more records can be generated for each entity (e.g., each record corresponding to a different entity or being shared across entities). Upon receiving a communication with data from a component (or facility), the record service can identify a corresponding record and update the record to include the data (or processed version thereof). In some examples, the record service provides data to transformative processing engine 108.

Irrespective of the type of facility, facility 110 may update data, maintain data, and communicate data to transformative processing engine 108. At least some of the data may be stored local to facility 110.

A user interacting with a user device 104 can include, for example, a client customer, client agent and/or a third party. A user may interact with user device 104 and/or component 102 so as to, for example, facilitate or initiate data collection (e.g., by a component 102), provide data, initiate transmission of a data request, access data and/or initiate transmission of a data-processing or data-storage instruction. In some instances, one or more user devices 104 may operate according to a private and/or proprietary network or protocols. In other examples, one or more user devices 104 may operate on public networks. In any case, however, transformative processing engine 108 can have access to the one or more components and can communicate with them via a public, private, and/or proprietary network or protocols. The use of one or more private and/or proprietary protocols can enable secure transfer of data.

Figure 2:
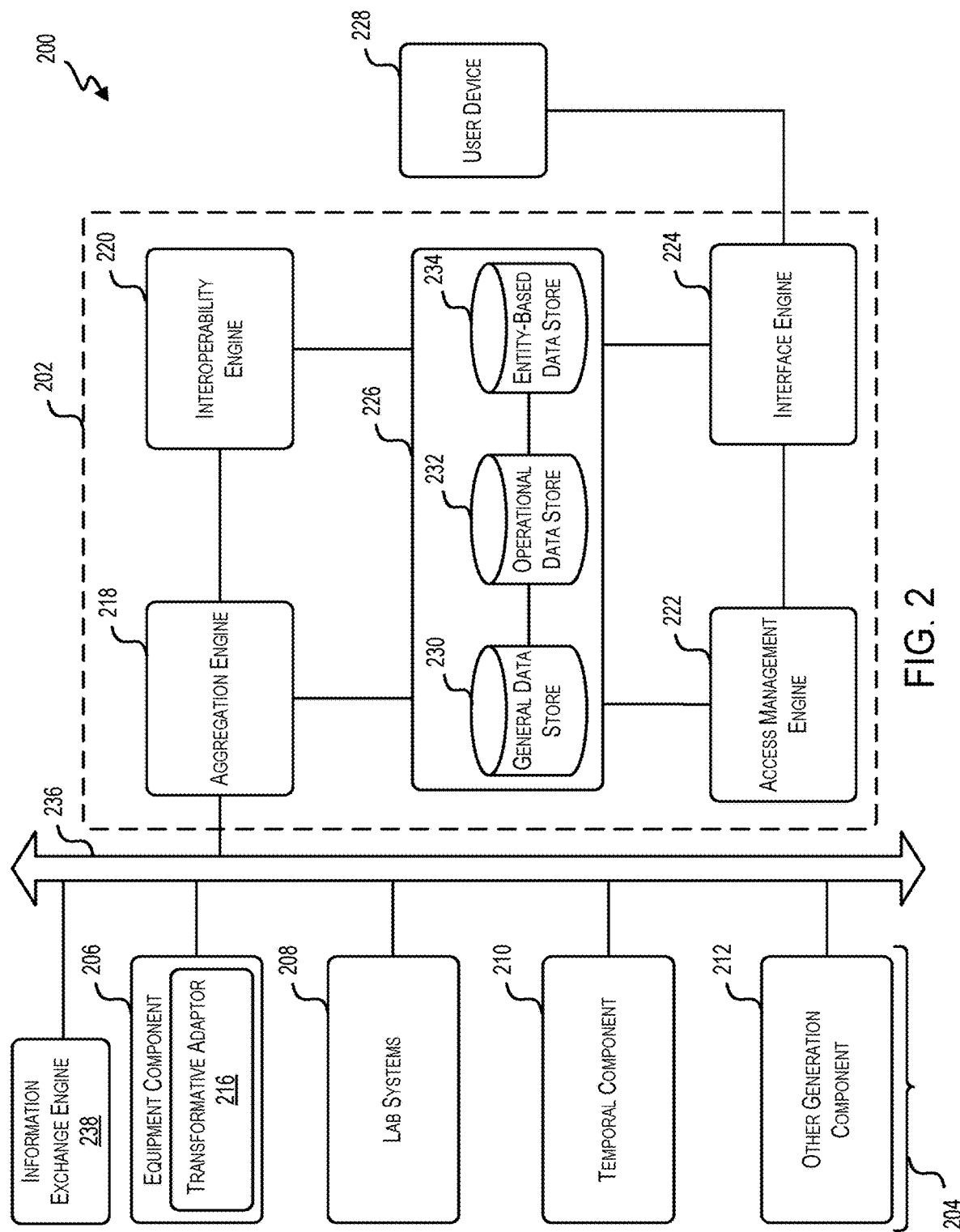
FIG. 2 is an example block diagram illustrating an interaction system in which techniques relating to aggregating data from disparate sources for anomaly event prediction may be implemented, according to at least one example.

Referring next to FIG. 2, a block diagram of an example of an interaction system 200 is shown. Interaction system 200 includes a transformative processing engine 202. Transformative processing engine 202 is an example of transformative processing engine 108 discussed with reference to FIG. 1. Interaction system 200 also includes one or more generation components 204. In particular, one or more generation components 204 include an equipment component 206, a lab systems component 208, a temporal component 210, and other generation component 212. One or more generation components 204 are examples of one or more components 102 discussed with reference to FIG. 1. In some examples, the data may pass to the transformative processing engine 202 via an information exchange service bus 236 (e.g., an enterprise service bus). In some examples, only a portion of the is passed via the information exchange service bus 236, while other portions are passed directly to the transformative processing engine 202 without first passing over the information exchange service bus 236.

Generally, one or more generation components 204 includes any suitable device or system capable of generating data in the context of an interaction system. For example, the other generation component 212 may include a sensor on a door, and equipment component 206 may include a sophisticated computer-controlled laser device. In either case, each generation component generates some type of data. For example, the data provided by the sensor may be used to address security concerns or assessing heating, ventilating, and air conditioning (HVAC) costs for an institution. The data provided by the laser device may have been provided while engaged in a procedure and may then be used by other entities in the future to decide how to use the device.

As discussed in further detail herein, data generated by one or more generation components 204 can be of a variety of formats, some of which may be proprietary. For example, a single component can generate data in multiple formats, different components can generate data in different formats, and/or different component types can result in generation of data in different formats. In some instances, formatting of a data can depend on a service having been provided, a user initiating data generation, a destination to receive the data, a location at which a service was provided, etc. In some examples, a typical interaction system includes thousands of generation components producing data in hundreds of formats. In order to harness the power that comes from such a large amount of data to make informed decisions, it is desirable that all, or at least a large portion of the data, is shared. Use of transformative processing engine 202 in accordance with techniques described herein may achieve this design making large amounts of data, in many different originating formats available to various types of users, via one or more interfaces. At least a portion of the data generated by the generation components 204 may be provided to the transformative processing engine 202. In some examples, each generation component 204 includes an agent that executes on the generation components 204 and determines which data to send to the transformative processing engine 202 and other engines described herein. In some examples, the generation components 204 provide data to the transformative processing engine 202 via a messaging bus (e.g., an information exchange service bus 236). The messaging bus, which may be included in the transformative processing engine 202 or separate, is able to see data that moves throughout the interaction system 200. The information exchange service bus 236 also includes a subscription registry that can be used to manage subscriptions to the information exchange service bus 236 for certain data (e.g., data having certain characteristics). The information exchange service bus 236 may send and/or direct data to certain other entities when appropriate as indicated by subscription records in the registry.

While one or more generation components 204 are illustrated adjacent to each other, it is understood that each may be located within one facility or that the components may be spread out among many facilities. In addition, in some examples, one or more generation components 204 belong to different clients.

Turning now to equipment component 206, this component includes any machine, contrivance, implant, or other similar related article, that is intended to aid in reaching a particular objective. In some instances, equipment component 206 includes one or more sensors to detect environmental or other stimuli. Equipment component 206 can include, for example, equipment to monitor a stimulus, detect stimulus changes, detect stimulus-indicative values, and so on. Exemplary equipment components 206 include an imaging device, a device that detects and characterizes electrical signals, a device that detects pressure, and/or a device that detects concentration of one or more particular elements, compounds and/or gases.

As illustrated, equipment component 206 includes transformative adaptor 216. In some examples, transformative adaptor 216 is a device that transforms, translates, converts, or otherwise adjusts output data from equipment component 206. For example, an equipment component 206 can be a scanner that outputs its results in format A, but the majority of other scanners in the interaction system output their results in format B. Transformative adaptor 216 may be implemented to convert or otherwise adjust the results in format A to conform closer to format B. For example, the conversion from format A to format B may be performed using a conversion rule, which may be user-define or learned. Transformative processing engine 202 may perform similar tasks as it relates to all data generated within interaction system 200. In this manner, transformative adaptor 216 can perform an initial step in the process of transformation, translation, conversion, or adjustment of the output of equipment component 206. In some examples, transformative adaptor 216 is implemented in hardware, software, or any suitable combination of both. In some examples, other transformative adaptors (not shown) may be implemented within others of one or more generation components 204. In some examples, equipment component 206 may not include transformative adaptor 216.

Lab systems component 208 includes any suitable laboratory equipment or system that is intended to analyze material, such as biological material. This includes, for example, laboratory equipment that analyzes biological samples; electric microscopes; ultracentrifuges; data collection devices, including Kymographs, sensors connected to a computer to collect data; monitoring devices; computers used to report results of lab tests, and other similar laboratory equipment. Each of the above-listed components generates data that is provided (directly or indirectly) to transformative processing engine 202.

Temporal component 210 may include any suitable computing devices used with respect to interaction system 200. For example, temporal component 210 can be configured to allocate a resource to a particular entity during a particular temporal window. Temporal component 210 can monitor a schedule for the resource and can identify one or more available temporal windows that may be secured by a particular entity. Upon receiving an indication, temporal component 210 may update a schedule of a resource to reflect that a particular temporal window is to be allocated for service of a particular entity.

Each of one or more generation components 204 and the user device 228 may include individual and/or shared storage systems, one or more processors, a user interface, a network connectivity device, and one or more ports. The storage system include memory that may be implemented, e.g., using magnetic storage media, flash memory, other semiconductor memory (e.g., DRAM, SRAM), or any other non transitory storage medium, or a combination of media, and can include volatile and/or non volatile media. The storage systems may also be configured to store computer-executable code or instructions for interacting with the user interface and/or for one or more applications programs, such as an application program for collecting data generated by the particular generation component.

The one or more processors may be configured to access the operating system and application programs stored within the storage systems, and may also be configured to execute such program code. The one or more processors can be implemented as one or more integrated circuits, e.g., one or more single-core or multi-core microprocessors or microcontrollers, examples of which are known in the art. In operation, the one or more processors can control the operation of the particular component. The one or more processors may access and execute the program code and at any given time.

The user interface can include any combination of input and output devices. In some instances, a user can operate input devices of the user interface to invoke the functionality of the particular component or user device. For example, the user interface may enable the user to view, hear, and/or otherwise experience output from component or user device via the output devices of the user interface. Examples of output devices include a display, speakers, and the like.

The network connectivity device may enable the component or user device to communicate with transformative processing engine 202 and other components or other user devices via one or more networks. The one or more networks may include any suitable combination of cable, cellular, radio, digital subscriber line, or any other suitable network, which may be wired and/or wireless. In some examples, the network connectivity device may enable the component or the user device to communicate wirelessly with various other components and/or transformative processing engine 202. For example, the components may include circuitry to enable data communication over a wireless medium, e.g., using near-field communication (NFC), Bluetooth Low Energy, Bluetooth® (a family of standards promulgated by Bluetooth SIG, Inc.), Zigbee, Wi Fi (IEEE 802.11 family standards), or other protocols for wireless data communication.

The one or more ports may enable the component or the user device to receive data from one or more sensors. The sensors may be any suitable type of sensor to capture data. Such captured data may be shared with transformative processing engine 202 in accordance with techniques described herein. In some examples, the sensors may also be configured to detect the location and other details about the component or the user device. In some examples, the component and the user device may include global positioning chips that are configured to determine a geolocation.

Transformative processing engine 202 includes an aggregation engine 218, an interoperability engine 220, an access management engine 222, an interface engine 224, and a data store 226. Generally aggregation engine 218 is configured to collect data from multiple communications. The data may be from one or multiple generation components 204 and/or may be of same or different formats. Aggregation engine 218 may be configured to perform one or more operations on the collected data. For example, aggregation engine 218 may tag data, log data, perform protocol conversion, and may support one-to-many communications. The collection may be asynchronous. In some examples, the data has been saved locally in connection with one or more generation components 204 in many different formats having many different data structures.

Aggregation engine 218 can identify data to be aggregated based on, for example, intra-communication data, a current time, a source generation component, and/or one or more aggregation rules. For example, an aggregation rule may specify that data is to be aggregated across all communications that include content with a same entity identifier. An aggregation may be dynamic. For example, aggregated data may reflect that from within a most recent 12-hour period. Thus, an aggregation may be updated in time to exclude older data from the aggregation and to include newer data.

Aggregation engine 218 can be configured to provide data from one or more communications to interoperability engine 220. Interoperability engine 220 can be configured to perform one or more operations on the received data and store it in data store 226. For example, interoperability engine 220 may perform semantic tagging and indexing of data. This may include extracting field values from data, categorizing data (e.g., by type of data, characteristic of an entity, location of facility, characteristic of facility, and the like), anonymizing or partially-anonymizing data, and the like. Interoperability engine 220 may also include a high availability cache, an alerts engine, and a rules engine. In some examples, interoperability engine 220 operates synchronously.

From interoperability engine 220, data flows to data store 226. Data store 226 (and any other data store discussed herein) may include one or more data stores, which may be distributed throughout two or more different locations (e.g., present on different devices, which can include devices of different entities and/or a cloud server). In some examples, data store 226 includes a general data store 230, an operational data store 232, and an entity-based data store 234. Within each of the data stores 230, 232, and 234 is stored data. Depending on the structure of the particular data store, certain data stores may include rules for reading and writing. The data stores 230, 232, and 234 may include records, tables, arrays, and the like, which may be relational or non-relational. Depending on the data store, records for individual entities, business and analytics information, output data from one or more generation components 204, and the like may be retained. The data within the data stores 230, 232, and 234 include elements or tags such that a particular data (e.g., for a single entity, protocol, etc.) can be retrieved.

Access management engine 222 is configured to manage access to features of transformative processing engine 202, including access to the data retained in data store 226. For example, access management engine 222 may verify that a user device such as user device 228 is authorized to access data store 226. To verify the user device 228, access management engine 222 may require that a user of the user device 228 input a username and password, have a profile associated with the interaction system, and the like. Access management engine 222 may also verify that the user device 228 has an IP address or geographical location that corresponds to an authorized list, that the user device 228 includes a plug-in for properly accessing the data store 226, that the user device 228 is running certain applications required to access the data store 226, and the like.

Interface engine 224 is configured to retrieve the data from data store 226 and provide one or more interfaces for interacting with elements of transformative processing engine 202. For example, interface engine 224 includes an interface by which an application running on user device 228 can access portions of data within data store 226.

As described herein, an information exchange engine 238 shares a network connection with the information exchange service bus 236. The information exchange engine 238 is configured to monitor data (e.g., messages) that is passed over the information exchange service bus 236 and, from the monitored data, select certain portions to provide to one or more authorized user devices. The information exchange engine 238 is also configured to route inbound messages and route outbound messages, as described herein. The information exchange engine 238 is also configured to generate customized messages based on dependent user data.

Figure 3:
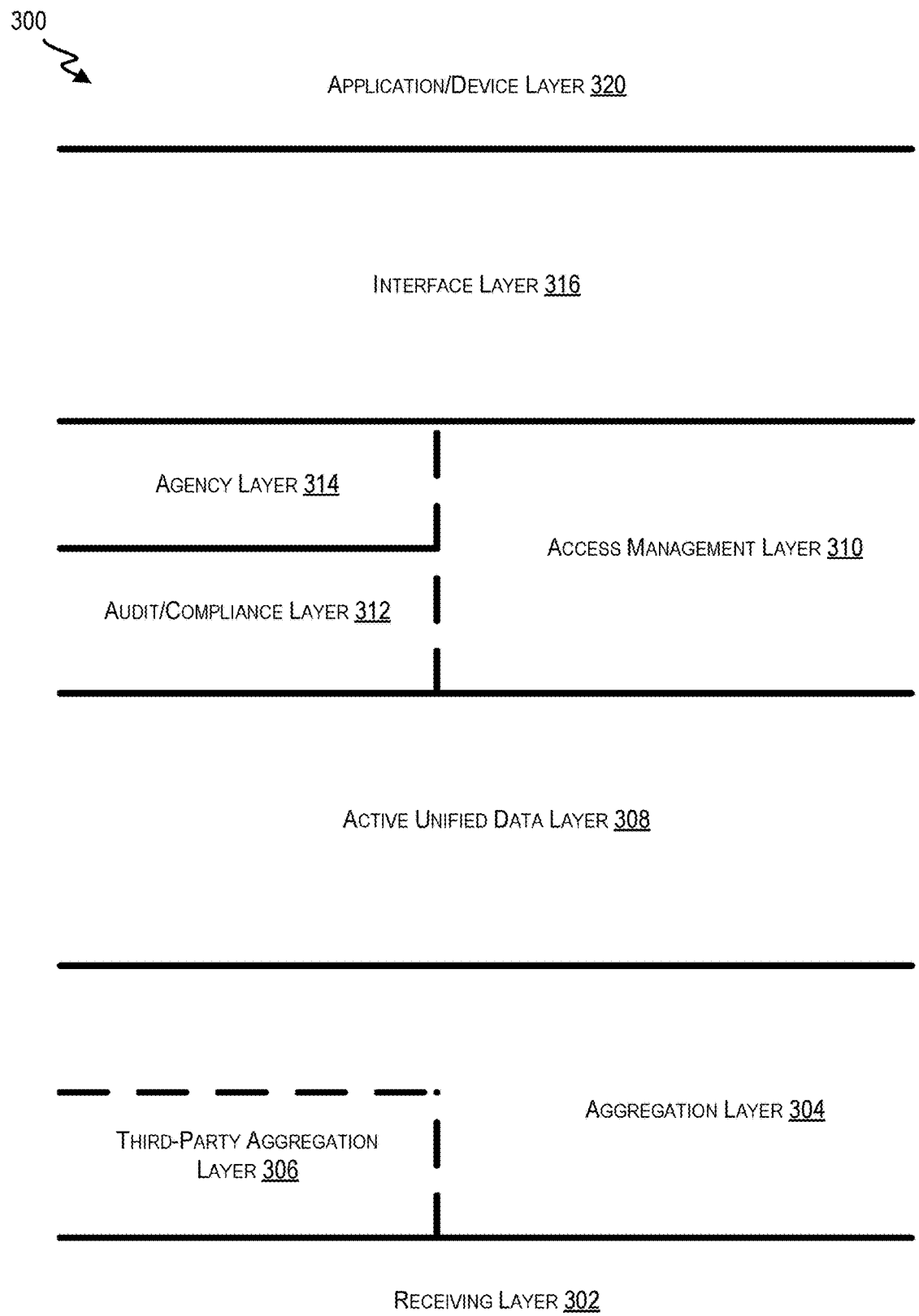
FIG. 3 is an example schematic model illustrating a network communication model in which techniques relating to aggregating data from disparate sources for anomaly event prediction may be implemented, according to at least one example.

Turning next to FIG. 3, an architecture stack 300 is shown. In some examples, techniques relating management of data are implemented in accordance with architecture stack 300. And while architecture stack 300 is illustrated as having a particular structure, it is understood that other structures, including those with more or less layers than illustrated, is within the scope of this specification. In some examples, architecture stack 300 is implemented across an interaction system having a plurality of systems belonging to the same client or spread across different clients. Thus, architecture stack 300 can be used to integrate different systems of different organizations, entities, and the like and to provide a fluid sharing of information among elements within the interaction system and without the interaction system. In some instances, a multi-layer part of architecture stack 300 is implemented at a single system or device within an interaction system.

The different layers of architecture stack 300 will be described generally with reference to FIG. 3 and in detail with reference to subsequent figures. Architecture stack 300 includes a receiving layer 302 as the bottom-most layer. Receiving layer 302 includes receiving data from elements that share data with other elements within an aggregation layer 304. For example, as detailed herein, receiving layer 302 can include receiving data from generation components that generate data. As such, receiving layer 302 is where data that has been created is received. In some examples, the data within receiving layer 302 may be in its raw formats. The output may then be transmitted to aggregation layer 304. In some examples, components of receiving layer 302 may have complimentary layers to facilitate data transfer. For example, the components may include a data generation and/or a data transmission layer for providing data to receiving layer 302.

Elements of aggregation layer 304 aggregate the data generated by the elements of receiving layer 302. For example, the elements of aggregation layer 304 may include aggregation engines that collect data from generation components located within receiving layer 302. Such aggregation may be performed periodically, in response to a user request, according to a schedule, or in any other suitable manner. In some examples, data of aggregation layer 304 may be aggregated according to input and/or rules and may aggregate across records pertaining to, e.g., a facility, entity, time period, characteristic (e.g., demographic characteristic or condition), outcome, and any other suitable input and/or rules. The aggregation may include compiling the data, generating a distribution, generating a statistic pertaining to the data (e.g., average, median, extremum, or variance), converting the data, transforming the data to different formats, and the like.

Next, architecture stack 300 includes an active unified data layer 308. Elements of active unified data layer 308 receive data from the elements of the other layers and store such data in a unified manner. In some examples, this may include storing the data in a manner that allows for later searching and retrieval using a defined set of method calls, techniques, and or procedures. For example, the data may be stored such that a different application can access the data in a standard or unified manner. Thus, elements of active unified data layer 308 may receive information collected or generated within aggregation layer 304 and make certain adjustments to the data (e.g., translations, tagging, indexing, creation of rules for accessing the data, conversion of formatting of the data, generation of compressed versions, and the like) prior to retaining the data within one or more data stores accessible within active unified data layer 308.

Architecture stack 300 also includes an access management layer 310, which can include an audit/compliance layer 312 and/or an agency layer 314. Access management layer 310 includes elements to manage access to the data. For example, access management layer 310 may include elements to verify user login credentials, IP addresses associated with a user device, and the like prior to granting the user access to data stored within active unified data layer 308.

Audit/compliance layer 312 includes elements to audit other elements of architecture stack 300 and ensure compliance with operating procedures. For example, this may include tracking and monitoring the other elements of access management layer 310.

Agency layer 314 includes an access location (e.g., a virtual private network, a data feed, or the like) for elements of agencies that are interested in the operations of the interaction system in which architecture stack 300 is implemented. For example, agency layer 314 may allow a governmental entity access to some elements within architecture stack 300. This may be achieved by providing the governmental entity a direct conduit (perhaps by a virtual private network) to the elements of access management layer 310 and the data within active unified data layer 308. Audit/compliance layer 312 and agency layer 314 are sub-layers of access management layer 310.

Architecture stack 300 also includes interface layer 316. Interface layer 316 provides interfaces for users to interact with the other elements of architecture stack 300. For example, clients, entities, administrators, and others belonging to the interaction system may utilize one or more user devices (interacting within application/device layer 320) to access the data stored within active unified data layer 308. In some examples, the users may be unrelated to the interaction system (e.g., ordinary users, research universities, for profit and non-profit research organizations, organizations, and the like) and may use applications (not shown) to access the elements within architecture stack 300 via one or more interfaces (e.g., to access data stored within active unified data layer 308). Such applications may have been developed by the interaction system or by third-parties.

Finally, architecture stack 300 includes application/device layer 320. Application/device layer 320 includes user devices and applications for interacting with the other elements of architecture stack 300 via the elements of interface layer 316. For example, the applications may be web-based applications, entity portals, mobile applications, widgets, and the like for accessing the data. These applications may run on one or more user devices. The user devices may be any suitable user device as detailed herein.

Figure 4:
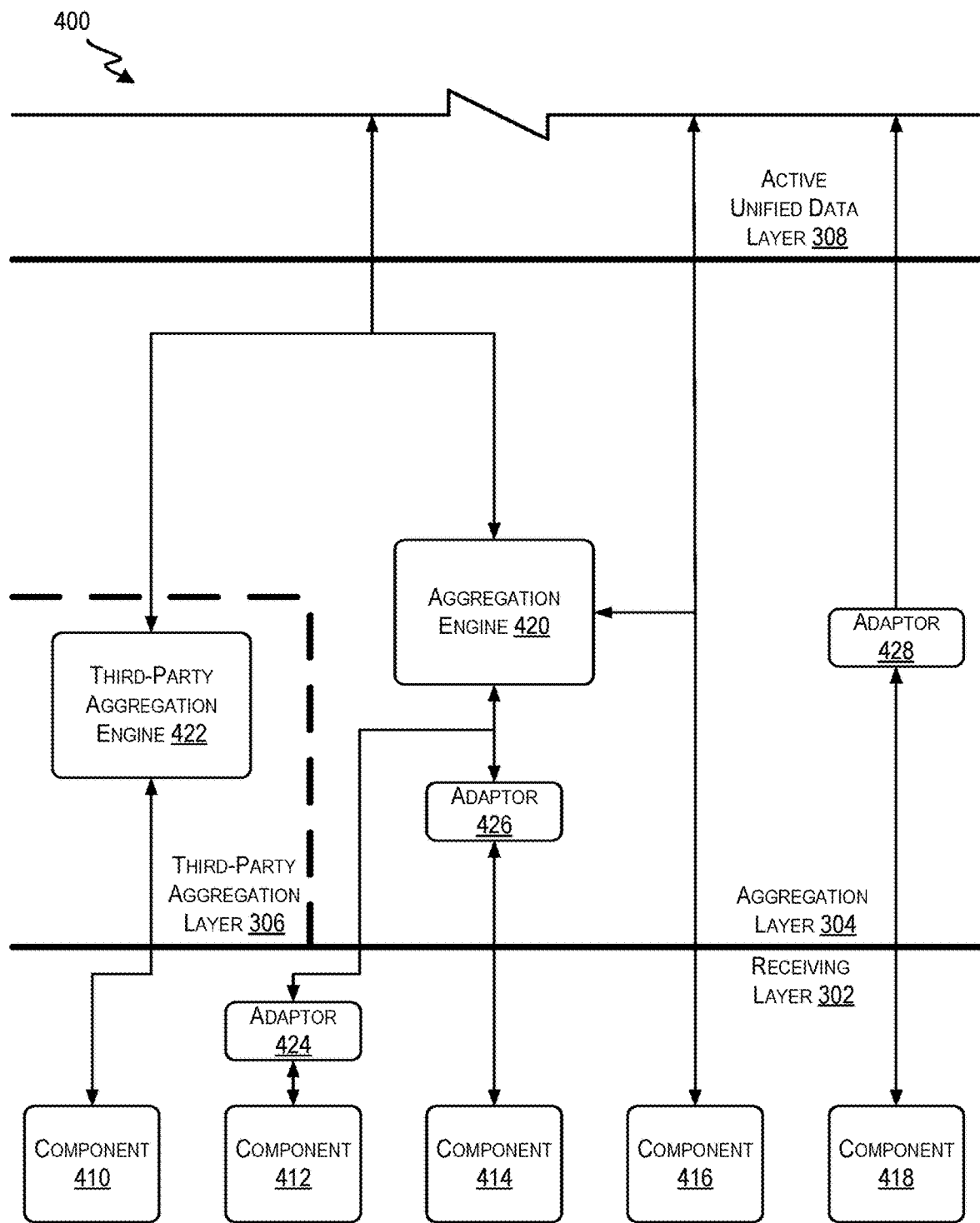
FIG. 4 is an example schematic model illustrating an aspect of the network communication model of FIG. 3 in more detail.

Turning next to FIG. 4, a diagram 400 is shown that depicts a portion of architecture stack 300 according to at least one example. In particular, the diagram 400 includes receiving layer 302, aggregation layer 304, aggregation layer 306, and a portion of active unified data layer 308. Receiving layer 302 receives data from one or more components 410-418. Components 410-418 are examples of one or more generation components 204. Components 410-418 may be spread across multiple facilities within a single or multiple clients. In some examples, components 410-418 may include complimentary layers to facilitate data transmission. For example, components 410-418 may include a transmission layer, generation layer, and/or a receiving layer to communicate data at receiving layer 302 and, in some examples, receive data from receiving layer 302.

In some instances, two or more of components 410-418 generate data according to different formats. The data can then be transformed, translated, or otherwise adjusted before an aggregation engine 420 (e.g., aggregation engine 218) or a third-party aggregation engine 422 (e.g., aggregation engine 218) collects the data. In some examples, the adjustment takes place within receiving layer 302. Thus, an adaptor 424 is associated with component 412 located in receiving layer 302. Adaptor 424 is an example of transformative adaptor 216. Adaptor 424 is implemented, as appropriate, in hardware, software, or any suitable combination of both. For example, transformative adaptor 216 may be a bolt-on adaptor that adjusts data as such data leaves component 412.

Other adaptors, such as adaptor 426 and adaptor 428, are implemented within aggregation layer 304. These adaptors can function in a similar manner as adaptor 424. In some examples, the data provided by component 414 is transmitted through adaptor 426 prior to being directed to aggregation engine 420. The data provided by component 416 is transmitted through aggregation layer 304 and/or enters aggregation engine 420 without having first traveled through an adaptor. The data provided by component 418 is transmitted through aggregation layer 304 and through adaptor 428. In some examples, component 418 provides for streaming of data. The data provided by component 410 is transmitted directly to third-party aggregation engine 422.

Aggregation engine 420 and third-party aggregation engine 422 function in a similar manner. In some examples, third-party aggregation engine 422 is operated by a different entity than the entity that operates aggregation engine 420 and may belong to different clients or a different interaction system. This may be because the data collected by third-party aggregation engine 422 differs in some way from the data collected by aggregation engine 420. In any event, aggregation engine 420 is configured to perform integration of data, including generic integration. For example, aggregation engine 420 performs one or more operations on data including tagging, logging, and protocol conversion. Aggregation engine 420 also supports one-to-many communications of data. In some examples, data flows between aggregation engine 420, the third-party aggregation engine 422, and some of components 410-418 and elements of active unified data layer 308.

The diagram 400 also includes the information exchange service bus 236 and the information exchange engine 238. As introduced herein, messages passing through the aggregation layer 304 can pass over the information exchange service bus 236. In this manner, the information exchange engine 238 can access the messages, route the messages, and/or customize the messages.

Figure 5:
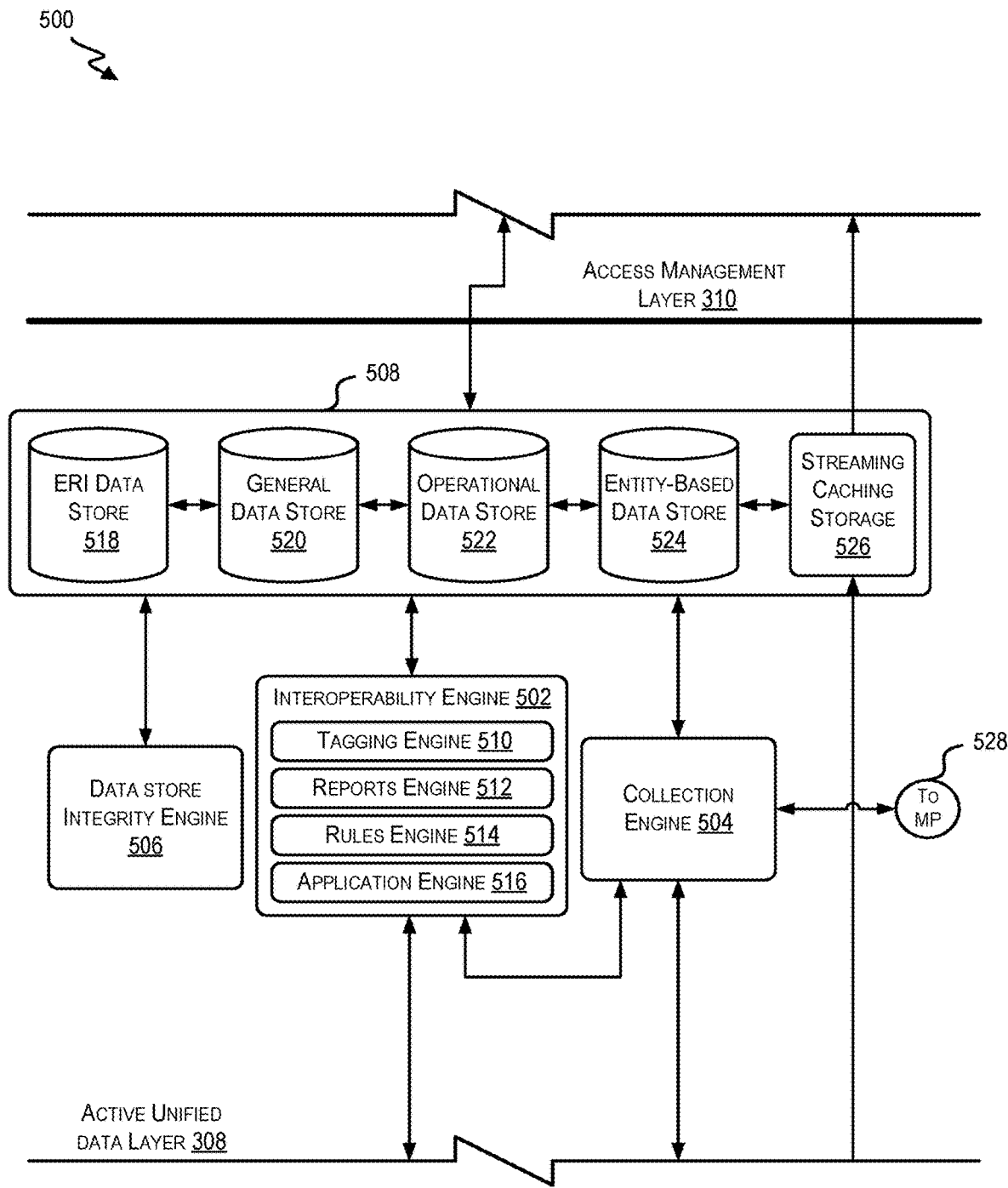
FIG. 5 is an example schematic model illustrating an aspect of the network communication model of FIG. 3 in more detail.

Referring next to FIG. 5, a diagram 500 is shown that depicts a portion of architecture stack 300 according to at least one example. In particular, diagram 500 includes active unified data layer 308 and a portion of access management layer 310. Active unified data layer 308, as illustrated in diagram 500, includes an interoperability engine 502 (e.g., interoperability engine 220), a collection engine 504, a data store integrity engine 506, and a data store 508 (e.g., data store 226). Generally, interoperability engine 502 receives data from elements within aggregation layer 304 (e.g., from aggregation engine 420) and performs one or more operations with respect to the data. Interoperability engine 502 also facilitates storage of at least a portion of the processed information in data store 508.

Collection engine 504 is configured to generate message indicators identifying flows of data by and between elements of an interaction system implemented using the techniques described herein. The flows of information include messages which include data, and the message indicators include unique message identifiers that can be used to identify the messages. The unique message identifiers include information that can be used to uniquely identify the messages. For example, a unique message identifier for a particular message can include a concatenation of the following information stored in a table: a source application, a facility, a message type, and a message control identification (ID). The unique message identifier can also be the message control ID. The unique message identifier may be created as messages including data are transmitted from aggregation layer 304.

In some examples, the table also includes information for tracking the progress of the message from an origination node to a destination node. For example, typically when a message (e.g., any communication of data) is first received by transformative processing engine 108 (e.g., interoperability engine 502), management engine 106 (e.g., collection engine 504 of management engine 106) may generate a unique identifier for the message in order to track that message as it moves throughout the interaction system. The unique identifier may be included in the header of the message such that when the next node (e.g., component, device, server, etc.) after transformative processing engine 108 receives the message, that node can report back to management engine 106 that it saw the message. In this manner, management engine 106 may track messages from end-to-end for the life of the message.

In one example, the messages are requests. The requests may be generated based om user input at one of the components. The requests may be received by transformative processing engine 108 and integrated into the system. In some examples, management engine 106 may be notified that the requests have been received and may therefore be configured to generate message IDs for each request. These message IDs may then be associated with each of the requests. As the requests continue to move throughout the interaction system (e.g., away from transformative processing engine 108), management engine 106 may track their movement using the message IDs. If one of the requests does not arrive at its destination, management engine 106 may determine why the request was stopped. In some examples, this cause may be hardware related (e.g., an unplugged Ethernet cable, a broken router, etc.), software related (e.g., a router routing to the wrong location), or any other reason for orders not arriving at their correct destination.

In some examples, management engine 106 (e.g., collection engine 504 of management engine 106) may receive the message and/or message identifier directly from one of components 410-418. For example, one of components 410-416 may be configured to generate the unique message identifier and/or communicate directly with management engine 106. The message also may travel via one or more intermediate nodes on its way to the destination node. In some examples, a node is a component such as components 410-418, which may be running an application. In some examples, the unique identifier and the routing of the message to its destination may be stored in a table that also includes: a geolocation of each node, a network from which the message originated, a type of node, the unique node identifier, and a time associated with the message leaving the origination node. In some examples, collection engine 504 provides unique message identifiers to other elements of the interaction system to monitor the messages as they move throughout the interaction system. Collection engine 504 also provides a portion of the unique message identifiers to a management platform (indicated by a circle 528) for further analysis of the message identifiers. Such analyses may include reconciliation of lost messages, latency reporting, audit management and compliance, and other such analyses.

As mentioned previously, interoperability engine 502 is configured to store data in data store 508. A plurality of sub-engines 510-516 of interoperability engine 502 are configured to perform operations relating to storing data in data store 508.

Interoperability engine 502 includes a tagging engine 510 configured to perform semantic tagging and indexing of data. Tagging engine 510 therefore is configured to receive data, read metadata associated with the data, semantically scan the content of the data, and associate one or more tags with the data. Tagging engine 510 may therefore have access to hundreds, thousands, or even more possible tags. These tags may have been input by users, learned, pre-defined, generated by outside third-party mapping sources, and/or gathered from other components and/or data stores of the interaction system. For example, if the data is a chart for an entity, the tagging engine may be configured to read any metadata associated with the chart to determine which tags may be appropriate to associate with the chart. From the metadata, tagging engine 510 may determine that the chart is for a type of entity by reading metadata indicating that an author field is populated with the name of another particular type of entity. Tagging engine 510 may have access to other data to compare the analyzed metadata against (e.g., to identify that the author's name corresponds to Dr. Brown who is an oncologist). Other examples, of metadata that may be included in one or more fields include author, document type, creation time and date, last update time and date, upload time and data, geographic location, unique ID associated with the client or facility where the data originated, and other similar fields. The tags may be stored in association with the data (e.g., the chart) and/or may be stored independent from the data but include an identifier such that when searching tags the data may be capable of population.

Continuing with the example from above, if the data is a chart for a first type of entity, tagging engine 510 may be configured to read the content of the chart to determine which tags may be appropriate to associate with the chart. For example, this may comprise analyzing the content of the chart (i.e., individual pages) semantically to look for artifacts (e.g., keywords, phrases, and the like) in the content. These artifacts may be identified by tagging engine 510 and used to decide which tags to associate with the document. In some examples, semantic scanning may involve filtering out words (e.g., articles, such as "a" and "the"), phrases, and the like. Similar to the reading of metadata, the tags may be pre-defined, user-defined, learned, and the like. In some examples, reading metadata associated with messages may provide meaning and/or give context to the particular record of data. This meaning and/or context may assist tagging engine 510 to determine one or more tags to associate with the data. The tags may be chosen, for example, based on values of particular fields in the data, detecting a frequency of one or more words in a document or metadata and/or of a set of related words (e.g., tagging a record with "cancer" upon detecting words such as tumor, metastasize, chemotherapy, radiation, oncology, malignant, stage 3, etc.). In this manner, tagging engine 510 may also index portions of the data within one or more data stores of data store 508. In some examples, such indexing may be based in part on the selected tags.

Interoperability engine 502 also includes a reports engine 512 configured to generate one or more reports or alerts based on data. For example, reports engine 512 may generate reports when certain types of data are received or when data with certain characteristics is received. Reports engine 512 may also generate alerts. The reports and/or alerts generated by reports engine 512 may be outputted in the form of one or more communications to an administrator, an authorized user, or other similar user via a user device. Such communications can include, for example, signals, sirens, electronic notifications, popups, emails, and the like. Content of such communications may include information characterizing a performance metric, efficiency and/or outcomes; identifying concerning patterns; identifying losses of data; and the like. In some examples, the content is presented in the form of one or more documents, tables, figures, charts, graphs, and the like.

Interoperability engine 502 also includes a rules engine 514 configured to create and manage condition-response rules, alert/reports rules, data-formatting rules, data-sharing rules, transmission rules, aggregation rules, user authorization rules, and other similar rules. Such rules may be user-defined, fixed, learned by elements of the interaction system, and any combination of the foregoing. Finally, interoperability engine 502 includes an application engine 516 configured to provide service-oriented architecture web services.

Data store 508 includes an electronic record information data store 518 ("ERI data store 518"), a general data store 520, an operational data store 522, an entity-based data store 524, and a streaming caching storage 526. While data store 508 is illustrated as including a fixed number of data stores and storage elements, it is understood that data store 508 can include any suitable number of data stores and storage elements, including more than illustrated or less than illustrated.

In some examples, a data query script is provided to query a first data store and/or to obtain data for populating a data store. Such script could query a data store described herein (e.g., data store 508) and/or could be used to obtain data to populate a data store described herein (e.g., data store 508). In one instance, the script is configured to be repeatedly executed, so as to repeatedly draw data from a source data store. The retrieved data can then be formatted, filtered, sorted and/or processed and then stored, presented and/or otherwise used. In this manner, the script can be used to produce streaming analytics.

In some instances, the data query script, when executed, identifies each of the data stores of interest. Identifying the data stores of interest involves identifying at least a portion of data from the data stores simultaneously and/or sequentially. For example, the script can identify corresponding data stores (e.g., or components of a single data store or multiple data stores) that pertain to one or more similar variables but that differ in one or more other variables. Once the portion of the data from the data stores is identified, a representation of the identified data can be output to one or more files (e.g., Extensible Markup Language (XML) files) and/or in one or more formats. Such outputs can then be used to access the data within one or more relational database accessible using Structured Query Language (SQL). Queries made using SQL can be made sequentially or in parallel. Results from an SQL query may be stored in a separate database or in an XML file that may be updated either in part or as a whole. The data query script may be executed periodically, in accordance with a user-defined rule, in accordance with a machine-defined or machine-learned rule, and in other suitable manner.

Within ERI record data store 518 is retained data. In some examples, the information within ERI record data store 518 is organized according to entity identifying information. Thus, ERI record data store 518, in some examples, includes individually identifiable information. But it may also include de-identified information.

Within general data store 520 is retained data. The data may be stored in a relational database format or in any other suitable format. Thus, the data within general data store 520 may be retained in a data structure that includes one or more tables capable of accessing each other. In some examples, general data store 520 includes a subset of the information that is included in operational data store 522.

Within operational data store 522 is retained data in a relational database format. Thus, the data within operational data store 522 may be retained in a data structure that includes one or more data structures (e.g., tables) capable of accessing each other. Operational data store 522 is an example of an operational data warehouse. In operational data store 522 is joined many different types of data. In some examples, the operational data store 522 includes data pertaining to decision making as discussed herein and other data typically used.

Within entity-based data store 524 is retained data in a non-relational database format. Thus, the data within entity-based data store 524 may be retained in a structure other than tables. Such structure may be appropriate for large and complex data sets. In some examples, entity-based data store 524 (or any other data store) may be a unified system, which may include: a document-centric, schema-agnostic, structure-aware, clustered, transactional, secure, database server with built-in search and a full suite of application services. An example of such a unified system may be Marklogic. Entity-based data store 524 can support data aggregation, data organization, data indexing, data tagging and mapping to semantic standards, concept matching, concept extraction, machine learning algorithms, concept discovery, concept mining, and transformation of record information. In some examples, entity-based data store 524 includes data pertaining to decision making (similar to general data store 520) as discussed that is organized and accessed in a different manner. For example, the data within entity-based data store 524 may be optimized for providing and receiving information over one or more information exchanges. In some examples, entity-based data store 524 includes a subset of the information that is included in operational data store 522.

Finally, in some examples, streaming caching storage 526 is a streaming data cache data store. As discussed previously, certain components of components 410-418 may support streaming data to other components or user devices. Streaming caching storage 526 is a location where streaming data can be cached. For example, assume that component 418 is a piece of equipment operating at Location A and that a user using a computer in Location B desires to view a live of substantially live stream of outputs of the piece of equipment. Component 418 can send a portion of data to streaming caching storage 526 which can retain the portion of the data for a certain period of time (e.g., 1 day). Thus, streaming caching storage 526 is configured to cache data that can be streamed.

Diagram 500 also includes data store integrity engine 506. In some examples, data store integrity engine 506 is configured to ensure integrity of the information within data store 508. For example, data store integrity engine 506 applies one or more rules to decide whether information within all or part of data store 508 should be scrubbed, removed, or adjusted. In this manner, confidence is increased that the information within data store 508 is accurate and current.

Figure 6:
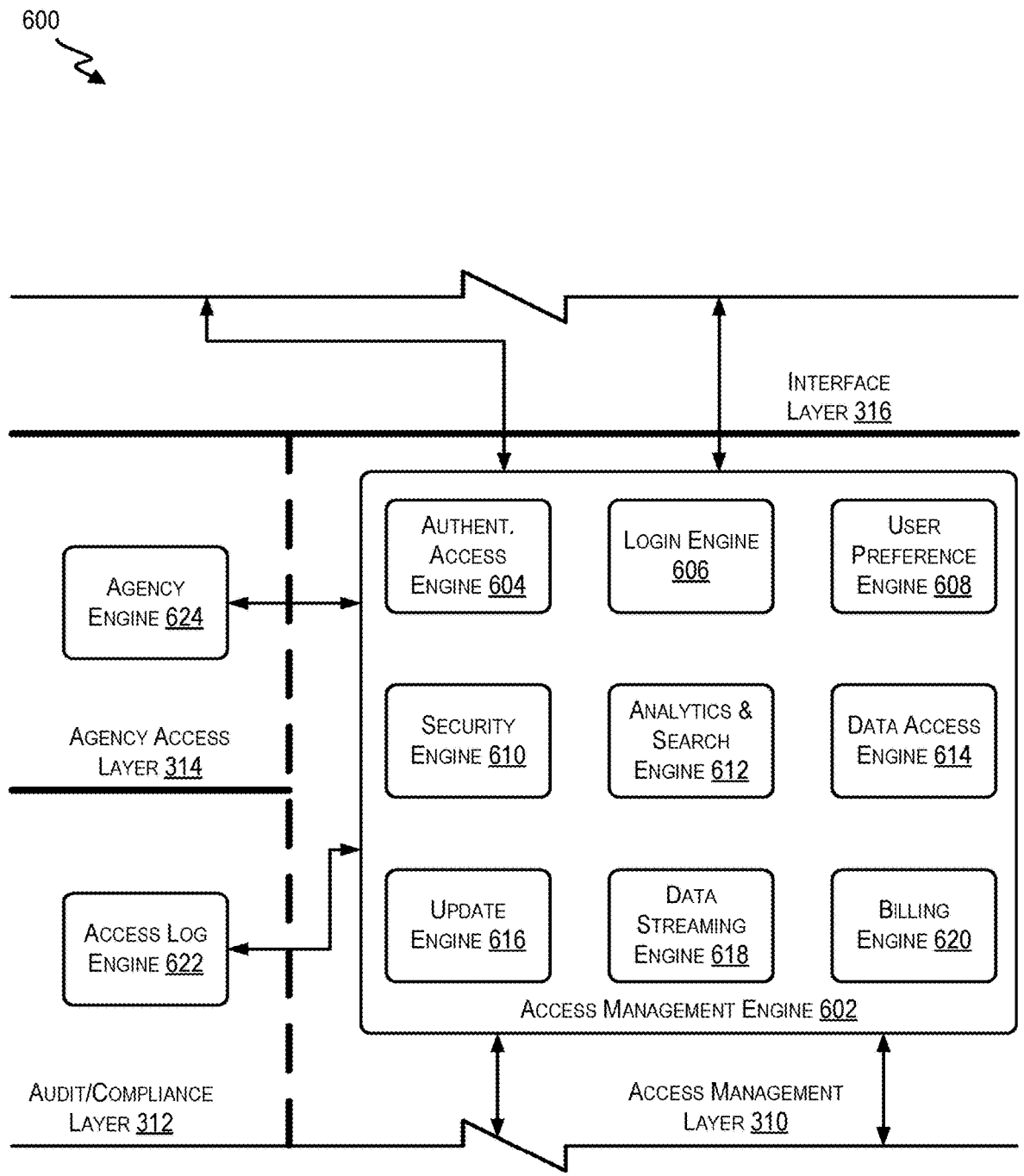
FIG. 6 is an example schematic model illustrating an aspect of the network communication model of FIG. 3 in more detail.

FIG. 6 shows a diagram 600 which depicts a portion of architecture stack 300 according to at least one example. In particular, the diagram 600 includes access management layer 310, audit/compliance layer 312, agency layer 314, and a portion of interface layer 316.

Access management layer 310, as illustrated in the diagram 600, includes an access management engine 602. Access management engine 602 is an example of access management engine 222. Generally, access management engine 602 can be configured to manage access to elements of transformative processing engine 202 by different components, applications, and user devices.

Access management engine 602 within access management layer 310 also provides functionality similar to an operating system. For example, access management engine 602 includes a plurality of engines configured to manage different aspects of interacting with elements of the interaction system. For example, a user who desires to access portions of data retained in data store 508, may do so by interacting with access management engine 602 using one or more applications (not shown). Thus, access management engine 602 includes a variety of engines to enable such interaction. The engines include, for example, an authentication access engine 604, a login engine 606, a user preference engine 608, a security engine 610, an analytics and search engine 612, a data access engine 614, an update engine 616, and a streaming data engine 618. The different engines of access management engine 602 can define routines, protocols, standards, and the like for interacting with elements of the interaction system.

Beginning first with authentication access engine 604, authentication access engine 604 evaluates the rules and conditions under which users may access elements of the interaction system; in particular, the conditions under which users may access data within data store 508. These rules and conditions may be user-defined (e.g., by an administrator or reviewer), learned over time, and/or may be dynamically updated and/or evaluated based on characteristics of the user or the user's device attempting to access the interaction system. The rules and conditions may indicate the types of users who have particular types of access within the interaction system. The type of access may also relate to the degree to which data is identified/de-identified. In some examples, a user desiring access to data provides certain identifying information and authentication access engine 604 authenticates an identity of the user.

Login engine 606 evaluates the rules and conditions under which users are able to log in to the interaction system or access applications associated with the interaction system. These rules and conditions may be user-defined (e.g., by an administrator), learned over time, and also may be dynamically updated and/or evaluated based on characteristics of the user or the user's device attempting to access the interaction system. Thus, while authentication access engine 604 evaluates the rules to determine which users may access the interaction system, login engine 606 evaluates the particular credentials, profiles, etc. of the users. For example, login engine 606 can confirm that an entered username (e.g., and password), provided biometric data or code or identifier in a scanned tag or badge matches that in an authorized user data structure.

Login engine 606 evaluates one or more user profiles associated with each authenticated user. In some examples, a user profile includes a username, password, and other information associated with the user. For example, a user profile may indicate characteristics about the user.

User preference engine 608 evaluates the rules and conditions under which user are able to store and update one or more user preferences corresponding to access of the interaction system or access to applications associated with the interaction system. These rules and conditions may be user-defined (e.g., by the user or administrator), and may include rules for default preferences. For example, using user preference engine 608, a user may indicate a format in which the user prefers to receive outputted information, display characteristics of a graphical user interface associated with the user, and other similar user preference settings. For example, the user may indicate that certain types of reports and/or alerts are to be sent to the user.

Security engine 610 evaluates the rules and conditions for ensuring the security of access to the elements of the interaction system. In some examples, these rules and conditions are determined by administrators of the interaction system. In some examples, security engine 610 provides a plurality of computer virus protection services. These services can be called up and implemented when accessing the interaction system or accessing applications associated with the interaction system. The rules and conditions may be based on roles, based on profiles, based on domains, and any other suitable security configuration. For example, because the interaction system may include sensitive data, security engine 610 may enforce a domain-based rule that protects certain sensitive information (e.g., identifying information).

Analytics and search engine 612 evaluates the rules and conditions under which users can search for data within the interaction system and access analytics relating to the interaction system. In some examples, these rules and conditions are user-defined or learned over time in accordance with search engine optimization techniques. For example, analytics and search engine 612 is used to search within data store 508 for particular data. Analytics and search engine 612 supports any conventional searching algorithms. For example, search engine 612 can be used to search within various fields and potential field values. In some examples, search engine 612 can provide analytics, such as statistics, graphs, distributions, and/or comparative analysis pertaining to particular entities and/or characteristics. Such information may be selected by a user and presented on a user interface.

Data access engine 614 evaluates the rules and conditions under which users may operation in order to access particular data within data store 508. In some examples, these rules and conditions are user-defined or learned over time. For example, data access engine 614 may indicate the routines, subroutines, or other logic needed for an application to access certain portions of data store 508. For example, while authentication access engine 604 and login engine 606 may manage which users can access parts of the interaction system, data access engine 614 may manage how authenticated users access data within data store 508. To this end, data access engine 614 may enforce and/or evaluate certain rules managing how users access different components of the interaction system. In some examples, data access engine 614 may be used to actually access data within data store 508 (e.g., extract, download, or otherwise access). In some examples, data access engine 614 may define procedures, protocols, and the like for accessing data. The protocols and procedures for accessing data access engine 614 (like the other engines of access management engine 602) may be provided to developers in the form of a software development kit (SDK). SDKs may enable developers write applications that can effectively communicate with elements (e.g., data store 508) of the interaction system. In particular, applications that can access a portion of the data stored within active unified data layer 308.

Update engine 616 evaluates the rules and conditions for providing updates to other engines within access management engine 602, plug-ins for applications that access the interaction system, and for other similar elements of the interaction system. For example, updates may be generated at runtimes, at defined time intervals, upon request by a user, upon receiving a threshold quantity of new or changed data. Once an update is performed, an interface may be refreshed, a report may be sent indicating that the update was successful or unsuccessful, or the like.

Streaming data engine 618 defines the rules and conditions for enabling streaming of data between components and user devices of the interaction system. For example, streaming data engine 618 may enable component 414 to stream data. Streamed data may include live or substantially live audio or video feeds, results of tests, output from equipment or devices, and any other suitable type of data capable of being streamed. In some examples, the data may be streamed to other components or user devices within the network or outside the network. In order to establish a streaming transmission, streaming data engine 618 may identify a streaming destination and a streaming origin. Next, streaming data engine 618 may pair the two and enable streaming. This may include allocated bandwidth within one or more network devices associated with the interaction system. Streaming data engine 618 may also adjust the quality of the streaming data based on the availability of bandwidth. In some examples, streaming data engine 618 may receive incoming streams (and continuously present the stream or monitor for particular data (e.g., exceeding a threshold, exhibiting an above-threshold change, having a particular value)).

Within audit/compliance layer 312 is located an access log engine 622. Access log engine 622 evaluates the rules and conditions for logging access to the interaction system by users, applications, devices, and the like. Logging access includes, in some examples, logging data conventionally collected by access log engines running in similar environments. Access log engine 622 can use this data to generate and transmit reports, for example, to stakeholders of the interaction system such that they can make informed decisions regarding that is accessing the interaction system and for what purposes.

Within agency layer 314 is located an agency engine 624. Agency engine 624 evaluates the rules and conditions under which agencies can access the interaction system. In some examples, agency engine 624 may be used to track one or more performance indicators identified by a government agency and/or to provide report instances of defined types of events. In some examples, a university is an agency that uses agency engine 624 to collect data pertaining to one or more studies. Agency engine 624 can collect the pertinent data, potentially format and/or analyze the data, and facilitate transmission of the data to the appropriate agency.

Figure 7:
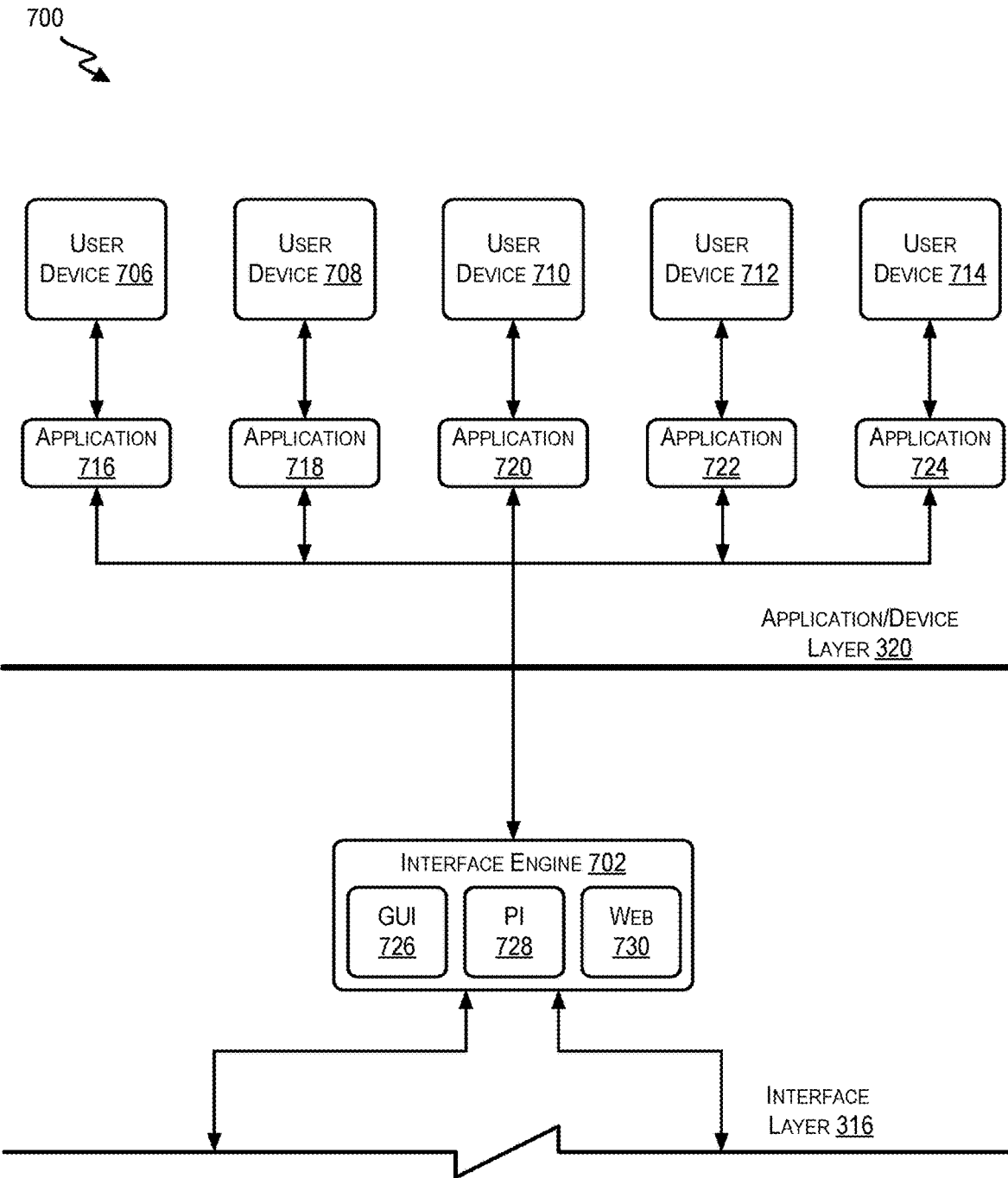
FIG. 7 is an example schematic model illustrating an aspect of the network communication model of FIG. 3 in more detail.

FIG. 7 shows a diagram 700 which depicts a portion of architecture stack 300 according to at least one example. In particular, diagram 700 includes interface layer 316, and application/device layer 320. Within interface layer 316 is located interface engine 702 (e.g., interface engine 224). Interface engine 702 is configured to generate one or more interfaces (e.g., graphical user interface 726, programmatic interface 728, and/or web interface 730) to enable data to flow to user devices 710, 712, and 714 via respective applications 720, 722, and 724. In some examples, the interfaces of interface engine 702 are embodied in hardware, software, or some combination of both. Within interface layer 316 communications and inputs directed to interacting with elements of access management layer 310 may be embodied.

Graphical user interface 726 is any suitable graphical user interface configured to interact with elements of the interaction system. Programmatic interface 728 includes an application programming interface, a programmatic user interface, and other similar interfaces for defining core functions for accessing elements of the interaction system. For example, programmatic interface 728 may specify software components in terms of their operations. Web interface 730 is any suitable web interface configured to interact with elements of the interaction system. Any of the interfaces described herein may be configured to receive user input, present dynamic presentations that depend on user input, and otherwise respond to user input. In some examples, such input may be provided via one or more input devices (e.g., a keyboard, touchscreen, joystick, mouse, microphone, devices capable of capturing inputs, and the like) operated by one or more users of user devices 706-714. Output may be provided via one or more output devices (e.g., a display or speaker).

Interface engine 702 is utilized by applications internal to the interaction system and external to the interaction system to access data. In some examples, the applications that are internal include applications that are developed for internal use by various entities associated with the interaction system. In some examples, the applications that are external to the interaction system include applications that are developed for external use by those that are not associated with the interaction system.

Generally, within application/device layer 320, applications 716-724 which communicate with other elements of architecture stack 300 using the interfaces generated by interface engine 702 are defined. This includes detailing how applications 716-724 are to interact with the interfaces generated by interface engine 702 for accessing data. For example, interacting may include accepting inputs at user devices 706-714 to access data and, in response, providing the data, prompts, or other types of interaction with one or more users of the user devices 706-714. Thus, applications 716-724 may be related to one or more of the interfaces generated by interface engine 702. For example, application 720 may be interact with a graphical user interface (whether generated by interface engine 702 or otherwise) to interact with other elements of the interaction system. Interacting may include receiving inputs at the graphical user interface via application 720, providing output data to the graphical user interface application 720, enabling interaction with other user devices, other applications, and other elements of the interaction system, and the like. For example, some of the inputs may pertain to aggregation of data. These inputs may include, for example, types of data to aggregate, aggregation parameters, filters of interested data, keywords of interested data, selections of particular data, inputs relating to presentation of the data on the graphical user interface, and the like. Providing output data may include providing the aggregated data on the graphical user interface, outputting the information to one of the other user devices 706-714 running one of the other applications 716-724.

Turning now to the details of applications 720, 722, and 724. In some examples, applications 720, 722, and 724 include a variety of different applications that can be designed for particular users and/or uses. In one example, application 720 includes dashboards, widgets, windows, icons, and the like that are customized for a particular entity. In some examples, application 720 may present different data depending on a focus of the entity and protected information associated with the entity. In this manner, application 720 adapts and automatically adjusts depending on the context in which the entity is using the application. Application 720 may be configured to receive input, adjust presentations, present unprompted alerts, adjust display of content, move more relevant content to the foreground, move less relevant content to the background, and/or populate forms for the entity.

In another example, application 722 may be specific for nurses or types of nurses. In this example, application 722 may include dashboards, widgets, windows, icons, and the like that are customized to individual nurses. Similar to the example discussed above pertaining to the user, in some examples, application 724 may present different data depending on a position of the nurse. In this manner, application 722 adapts and automatically adjusts depending on the context in which the nurse is using the application. For example, the nurse may receive data, such as test results.

In some examples, application 724 may be a multi-role application for administrators and is used to manage entities constitute the population of the entities or organizations within the interaction system. Similar to the other examples discussed, in some examples, application 724 may present different data depending on a role of the user who is using application 724. In this manner, application 724 adapts and automatically adjusts depending on characteristics of the user who is using application 724. In this manner, application 724 can provide different data depending on the role of the user. For example, whether data presented includes identifiable or de-identified information may depend on a position of the user.

716 and 718 shown in connection with interface engine 702 are applications developed by third-parties. In some examples, such applications include any suitable application that benefits from accessing data. The interaction system may include data pertaining to hundreds of thousands of entities. Having data pertaining to so many entities presents security concerns. For example, much of the data may be identifying data. Accordingly, data that may be accessed by applications 716 and 718 may be limited. In some examples, an entity of the interaction system may use one of applications 716, 718 to access his or her own data. In this example, the identity of the entity may be verified in accordance with techniques described herein.

User devices 706-714 are any suitable user devices capable of running applications 716-724. User devices 706-714 are examples of the user device 228. In some examples, the user devices include: mobile phones, tablet computers, laptop computers, wearable mobile devices, desktop computers, set-top boxes, pagers, and other similar user devices. In some examples, at least some of user devices 706-714 are the same devices as at least some of the one or more components 410-418. In some examples, user devices 706-714 may include complementary layers to application/device layer 320 and/or receiving layer 302. For example, user devices 706-714 may include a transmission layer, a generation layer, and/or a receiving layer to communicate data at application/device layer 320 and at receiving layer 302.

Figure 8:
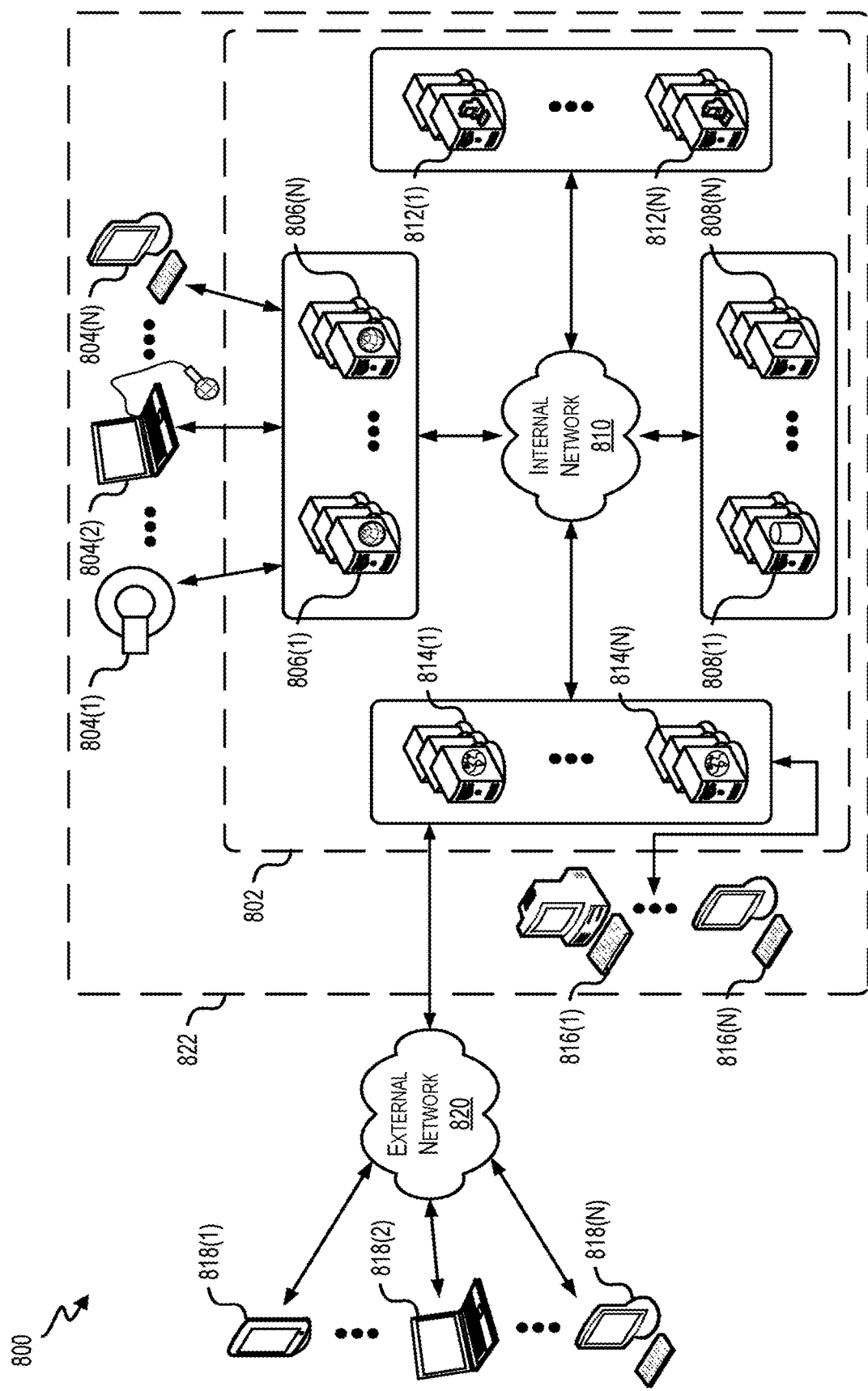
FIG. 8 is an example schematic architecture illustrating an interaction system in which techniques relating to aggregating data from disparate sources for anomaly event prediction may be implemented, according to at least one example.

Turning now to FIG. 8, an interaction system 800 is shown according to at least one example. Interaction system 800 includes an internal organization 822 including a transformative processing engine 802. The transformative processing engine 802 is an example of transformative processing engine 202 previously discussed. Interaction system 800 is illustrated as an example configuration for implementing the techniques described herein. In particular, a configuration of elements as illustrated in FIG. 8, at least in some examples, communicates according to the layers of architecture stack 300. For example, internal organization 822 includes generation components 804(1), 804(2), and 804(N) which provide data to aggregation servers 806(1)-806(N).

Generation components 804(1), 804(2), and 804(N) operate in accordance with receiving layer 302. In some examples, generation component 804(1) is a piece of equipment, generation component 804(2) is computer with a data collection device, a type of lab system, and generation component 804(N) is a terminal. Aggregation servers 806(1)-806(N) operate in accordance with aggregation layer 304. Aggregation servers 806(1)-806(N) share data with data storage servers 808(1)-808(N) via one or more internal network(s) 810. In some examples, internal network 810 is any suitable network capable of handling transmission of data. For example, internal network 810 may be any suitable combination of wired or wireless networks. In some examples, internal network 810 may include one or more secure networks. Data storage servers 808(1)-808(N) are configured to store data in accordance with active unified data layer 308. Data storage servers 808(1)-808(N) include database servers, file storage servers, and other similar data storage servers.

Access management servers 812(1)-812(N) manage access to the data retained in the data storage servers 808(1)-808(N). Access management servers 812(1)-812(N) communicate with the other elements of interaction system 800 via internal network 810 and in accordance with access management layer 310.

Interface servers 814(1)-814(N) provide one or more interfaces applications to interact with the other elements of interaction system 800. Interface servers 814(1)-814(N) provide the one or more interfaces and communicate with the other elements of interaction system 800 via internal network 810 and in accordance with interface layer 316. The interfaces generated by the interface servers 814(1)-814(N) can be used by internal user devices 816(1)-816(N) and external user devices 818(1), 818(2), and 818(N) to interact with elements of interaction system 800.

Internal user devices 816(1)-816(N) are examples of user devices 706-714. In some examples, internal user devices 816(1)-816(N) run applications via the interfaces generated by interface servers 814(1)-814(N). As an additional example, external user devices 818(1), 818(2), and 818(N) can run applications developed by third parties that access the other elements of interaction system 800 via the interfaces generated by interface servers 814(1)-814(N).

External user devices 818(1), 818(2), and 818(N) access the interfaces via external network 820. In some examples, external network 820 is an unsecured network such as the Internet. External user devices 818(1), 818(2), and 818(N) are examples of user devices 706-714. External user device 818(1) is a mobile device. In some examples, the mobile device may be configured to run an application to access interaction system 800. Similarly, the other external user devices 818(2)-818(N) run applications that enable them to access interaction system 800. While interaction system 800 is shown as implemented using discrete servers, it is understood that it may be implemented using virtual computing resources and/or in a web-based environment.

Figure 9:
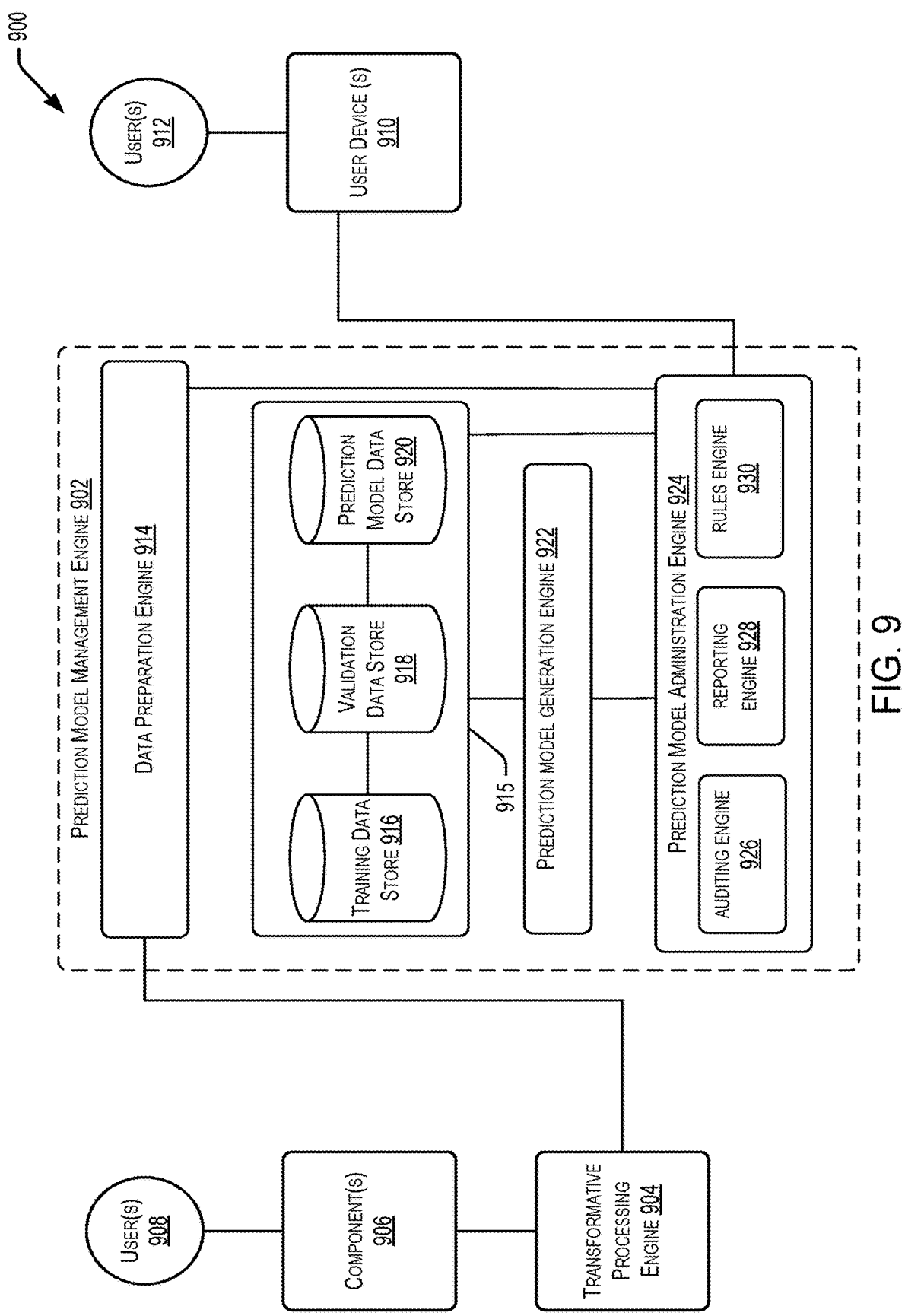
FIG. 9 is an example architecture illustrating a system in which techniques relating to providing a prediction that a user is associated with one or more anomaly events, according to at least one example.

Turning now to FIG. 9, a block diagram of an example of a service provider prediction system 900 is shown. In some examples, the service provider prediction system 900 is a component of (or connected to) a service management system (e.g., a service provider network) that is affiliated with a service organization. The service organization may include one or more service (e.g., service) facilities, which may each transmit data to the service management system. The service management system may include one or more other components as described in FIGS. 1-8 described herein. The service provider prediction system 900 of FIG. 9 includes a prediction model management engine 902. The service provider prediction system 900 further includes a transformative processing engine 904. The transformative processing engine 904 is an example of the transformative processing engine 108 discussed with reference to FIG. 1. The service provider prediction system 900 also includes one or more generation components 906, which may be similar to the one or more generation components 204 discussed in reference to FIG. 2. In some examples, the generation components 906 may receive data input from one or more users 908 (e.g., service technicians, etc.). The service provider prediction system 900 also includes one or more user devices 910 used by users 912 (e.g., user service providers (USPs) such as nurse consultants). The user device(s) 910 may be similar to user device 228 of FIG. 2 and/or user device 104 of FIG. 1. The transformative processing engine 904 and the user device(s) 910 may communicate with the prediction model management engine 902 using any suitable network connectivity device, as described earlier.

In some examples, the transformative processing engine 904 may receive service-related data generated by the generation components 906 (e.g., a lab systems component 208, service equipment component 206, other generation component 212, etc.). The service-related data (e.g., lab results) may be collected from one or more service facilities of a service organization. The data can further include an identification of a user (e.g., an authorized user or a dependent user) and/or other user-pertinent information (e.g., user service records, service history, genetic data, biometric data, actual or suspected diagnosis, and/or demographic information). The transformative processing engine 904 may receive the data in any suitable format and may transform the data into a format that is suitable for reception by the prediction model management engine 902. For example, the prediction model management engine 902 may access the transformed data via the interface engine 224 of the transformative processing engine 904. Data may be received by the prediction model management engine 902 using any suitable cadence (e.g., once a day, once an hour, once every minute, every few seconds, etc.). The data may be received (directly or indirectly) via either push or pull technology. In some examples, newly received data may be used to update (e.g., retrain) one or more prediction models of the prediction model management engine 902.

The prediction model management engine 902 includes a data preparation engine 914, a prediction model generation engine 922, a prediction model administration engine 924, and a data store 915. Generally, the data preparation engine 914 is configured to receive and process service-related data from the transformative processing engine 904. In some examples the data preparation engine 914 may prepare (e.g., further transform and/or segment) service-related data so that the data may be used to train and validate a prediction model. For example, a data set of service-related data may be split into different subsets by the data preparation engine 914. A training data subset may be generated that is used to train a particular prediction model (e.g., adjusting the weights between interconnected nodes of a neural network). In some examples, the same (or similar) training data subset may be used to train one or more prediction models utilizing different algorithms, and then a best model may be chosen. A cross-validation subset may also be generated that may be used to compare the performances of prediction algorithms that were created based on the training set. The cross-validation subset may be a separate set of data that is held back from training the model, and may be used to minimize overfitting of data (e.g., verifying that any increase in accuracy achieved over the training data set is not due to over fitting). A test subset (e.g., separate from the training subset and cross-validation subset) may also be used to determine how a particular prediction algorithm will perform on new data. In some examples, any suitable segmenting of data received from the transformative processing engine 904 may be determined by the data preparation engine 914 for training a prediction model.

As discussed further herein, different types of algorithms (e.g., machine learning algorithms) may be used to generate prediction models. For example, the prediction model management engine 902 may perform supervised or unsupervised learning to generate prediction models. Typically, especially in the case of supervised learning, as part of the training and validation processes, ground truth labels may be created for data samples and included in (or alongside) one or more of the subsets of data determined by the data preparation engine 914. A ground truth label may refer to information that is provided by direct observation, as opposed to information provided by inference. The ground truth label may be used to measure the accuracy of a training data set's classification. For example, a prediction model may be trained to predict whether a user has a particular condition (e.g., cancer). A ground truth label for a particular user may be determined based on an actual observed outcome of the particular user's condition (e.g., an authorized user confirms that the user has cancer). The training sample for that user may include other data (e.g., blood analysis, biometric data, etc.), which may be used as input to train a prediction model. The prediction that is output by the prediction model may be compared against the ground truth label to determine the accuracy of the prediction, and the comparison results may be used to adjust (e.g., learn) weights and/or parameters of the model accordingly.

In some examples, the data preparation engine 914 may perform semantic tagging and indexing of service-related data (e.g., categorizing data). The data preparation engine 914 may also determine if gaps exist in the pool of data samples, whereby new data should be obtained to increase training coverage. For example, some users' service records may omit an attribute (e.g., Body Mass Index (BMI)) which may be determined to be an important feature for training a particular prediction model. In this case, the data preparation engine 914 may tag these records as requiring attention and transmit a notification to a user device of a system administrator for further action. The data preparation engine 914 may also perform feature engineering, which may involve further transforming and/or extracting the data into a different form that is suitable for training a particular prediction model. For example, the data preparation engine 914 may receive raw data corresponding to pixels of an image (e.g., of a portion of a user's body). The data preparation engine 914 may then perform one or more operations to analyze the pixels of the image to generate a new feature from the raw data (e.g., a level of skin redness). This new feature may then be used as one of the inputs to a machine learning algorithm (e.g., predicting a type of body condition). It should be understood that, in some cases, the data preparation engine 914 may execute a previously generated prediction model in order to engineer a feature that may in turn be used to train another prediction model.

From the data preparation engine 914, data may flow to the data store 915. The data store (and any other data store discussed herein) may include one or more data stores, which may be distributed throughout two or more different locations (e.g., present on different devices, which can include devices of different entities and/or a cloud server). In some examples, the data store 915 includes a training data store 916, a validation data store 918, and a prediction model data store 920. Within each of the data stores 916, 918, and 920 is stored prediction model-related data. In some examples, the structure of one or more of the data stores 916, 918, or 920 may be similar to data store 226. The training data store 916 may contain training data that is used to train a prediction model. The training data may include multiple samples (e.g., based on user service records), and may include ground truth data for each sample. Different sets of training data may be created from the multiple samples (e.g., generating a new training data set on a predetermined time interval). The different training data sets may also be training data subsets that are randomly generated from an overall pool of training data samples, so as to reduce the risk of overfitting. The validation data store 918 may contain training data that is used to validate a prediction model. For example, the validation data store 918 may contain cross-validation and/or test data subsets that are generated from the pool of training data samples. The training data stored in the validation data store 918 may be determined and further curated based at least in part on the composition of the training data sets in the training data store (e.g., generating disjoint sets of data for increased accuracy during validation and testing). The prediction model data store 920 may contain one or more prediction models, which may be either trained or untrained prediction models. The trained prediction models may be generated from the prediction model generation engine 922, discussed further below. The prediction model data store 920 may further include parameters that may be used to train (or update) a prediction model. As a non-limiting example, this may include a type of loss function, a learning rate (e.g., how much to adjust data weights after each training iteration), a subsample size (e.g., indicating how many training samples should be used to train a new model), a number of nodes (e.g., in the case of a neural network), a number of leaves/levels (e.g., in the case of a decision tree), a number of trees (e.g., in the case of a boosted decision tree model), a learn rate, etc.

The prediction model generation engine 922 is configured to generate one or more trained prediction models based at least in part on data from the data store 915. A trained prediction model may be trained to identify which set of one or more categories a new observation (e.g., data from a user's service record) belongs. In the case of supervised learning, this may be based on the training set of data containing observations whose category membership is known (e.g., a user who is known to have a particular cancer, which observation may be recorded as a ground truth label). In the case of unsupervised learning, this may be based on grouping data into categories based on some measure of inherent similarity or distance (e.g., clustering). In either type of learning, a trained prediction model may classify an observation as a binary classification (e.g., patent has or does not have a condition) or a multiclass classification (e.g., user has a particular type condition of several possible condition types). In some examples, a trained prediction model may use observation data to output one or more classifications (e.g., assessments) about one or more respective aspects regarding a user's condition (e.g., a likelihood of a condition, a type of condition, a severity of condition, etc.). Each of these one or more classifications may be either binary or multiclass classifications. The classifications may include one or more values (e.g., a binary value, or a real number (between 0-1)) that indicate a likelihood of a particular classification being an accurate assessment.

The prediction model generation engine 922 may utilize one or more artificial intelligence techniques to generate a prediction model. As used herein, the term "artificial intelligence" (AI) refers to any suitable computer-implemented artificial intelligence technique including, but not limited to, machine learning (ML) (supervised or unsupervised), natural language processing, machine perception, computer vision, affective computing, statistical learning and classification, Bayesian network models and Kalman filters, reinforcement learning including neural networks, search algorithms and optimization algorithms (including evolutionary computing) and automated reasoning. Non-limiting examples of classification algorithms include use of hidden Markov models, decision trees (e.g., boosting decision trees, random forests), support vector machines, etc.

The prediction model administration engine 924 may be utilized to configure the prediction model management engine 902. In some examples, the prediction model administration engine 924 includes an auditing engine 926, a reporting engine 928, and a rules engine 930. The auditing engine 926 may include elements for tracking and monitoring the performance of a prediction model. For example, the auditing engine 926 may be configured (e.g., by a user device 910) to monitor precision and recall values (and/or sensitivity and specificity values) for a prediction model over time, as new data is received and input into the prediction model. The reporting engine 928 may include elements for generating one or more reports that are consumable by a user 912 via a user device 910. For example, the reporting engine 928 may execute one or more trained prediction models to generate a report for a one or more users. The report may indicate, for each user, a predicted classification of the user based on current user data (e.g., whether the user has a particular condition or not). The report may include other information (e.g., user demographics, user admission data, etc.), which may assist a user service coordinator in determining a course of service for the user. The reports engine 928 may also output reports on a periodic basis that indicate the performance of one or more prediction models, which may be used to determine whether a model should be retrained with updated data. The rules engine 930 may determine one or more rules for managing aspects of the prediction model management engine. For example, the rules engine 930 may receive input from a user device 910 that is used to configure the data preparation engine (e.g., add a new feature to the list of predictive features being tagged). The rules engine 930 may also be used to configure aspects of the data store 915 (e.g., controls for determining which data should be grouped into a training subset versus a test and/or cross-validation subset, how large a training sample subset should be, etc.). The rules engine 930 may also be used to configure aspects of the prediction model generation engine 922. For example, the rules engine 930 may receive input indicating when a new prediction model should be generated (e.g., on a predetermined cadence, using one or more ML algorithms with particular parameters, etc.).

Figure 10:
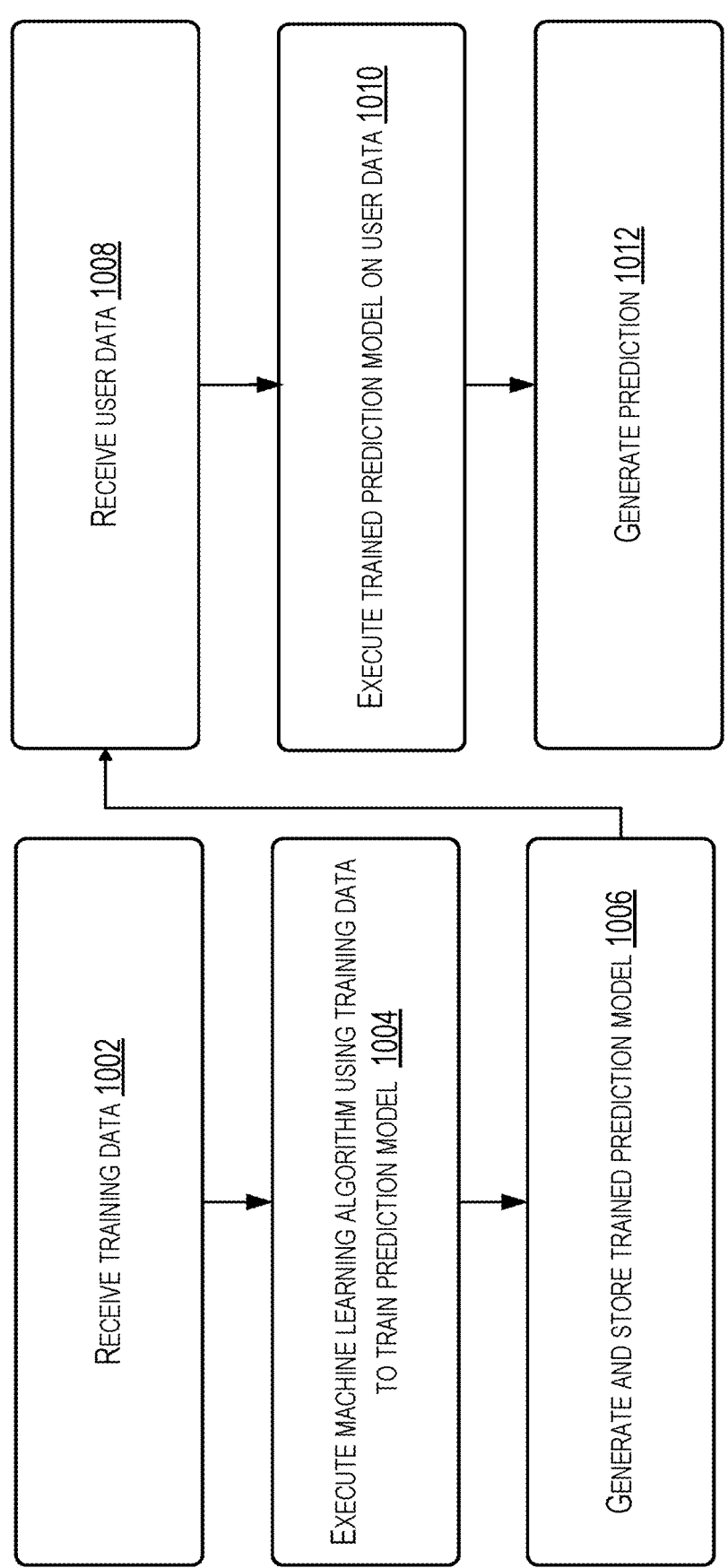
FIG. 10 is an example flowchart illustrating a process for providing a prediction that a user is associated with one or more anomaly events, according to at least one example.

Turning to FIG. 10, an example flow diagram is depicted for a computer system training a prediction model and executing the trained prediction model. The flow diagram may proceed in two phases: a training phase (blocks 1002-1006) and an execution phase that follows the training phase (blocks 1008-1012). In some examples, the computer system that performs the flow 1000 may correspond to the service provider prediction system 900 of FIG. 9.

Some or all of the flow 1000 (or any other processes described herein, or variations, and/or combinations thereof) may be performed under the control of one or more computer systems configured with executable instructions and may be implemented as code (e.g., executable instructions, one or more computer programs, or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Additionally, these processes are illustrated as logical flow diagrams, each operation of which represents a sequence of operations that can be implemented in hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be omitted or combined in any order and/or in parallel to implement the processes.

The example flow 1000 may start at block 1002, whereby the system may receive training data. In some examples, the training data may be generated from one or more generation components 204 (e.g., lab systems, other generation components, etc.). In some examples, the one or more generation components 204 may belong to different service providers (e.g., different service facilities) within a service organization. In some examples, the training data may be received from other sources outside the service organization (e.g., third party entities, government organizations). The training data may be associated with and/or derived from user data of users, for example, derived from user electronic service records. In some examples, a training data sample of the training data may include a plurality of data points that identify characteristics of a user, diagnoses and/or assessments made by service providers, associated service plans for the user made by the providers, associated outcomes of the user based on those service plans, condition indicators for the user, laboratory test results (e.g., from blood, urine, and/or other tests), and other suitable information. In some examples, the training data may indicate not only historical service data, corresponding to previous admissions of the user, but may also include present admission data, corresponding to a present admission of the user for a condition. In some embodiments, the user may correspond to a dependent user (e.g., a patient) or an authorized user (e.g., a physician, a nurse, etc.). The user data may be received in any suitable form, including, but not limited to, text, audio, video, digital images, and numerical values. The training data may be processed and/or transformed into a suitable form for training a prediction model, for example, by data preparation engine 914. In some examples, this may involve semantically tagging the data, segmenting the data into different subsets (e.g., training sets, cross-validation subsets, testing subsets, etc.), performing feature engineering to generate one or more features for training the prediction model, etc. The training data may be stored in a data store (e.g., data store 915) for future use in training a prediction model.

At block 1004, the system may execute a machine learning algorithm using the training data to train a prediction model. Any suitable machine learning algorithm may be used to train the prediction model, including supervised learning algorithms (e.g., logistic regressions, neural networks), unsupervised learning algorithms (e.g., K-means, Apriori algorithm), and/or reinforcement learning algorithms (e.g., Markov decision processes).

In a first non-limiting example of a supervised learning algorithm, a neural network machine learning algorithm may be used to generate a prediction model using a set of inputs (e.g., training data) that includes one or more features, which in some cases may be measurable properties derived from user data (e.g., blood cell count, blood pressure, age, etc.). Any suitable number of features may be used as input to generate the prediction model. Using this technique, the set of inputs may be used as an input layer and the set of outputs may be used as an output layer. In this technique, the input layer may be connected to the output layer via one or more hidden layers. Each layer may include a set of one or more nodes, whereby each node may represent a piece of information. The generated prediction model may include a number of interconnections between the hidden layers and the input layer and/or output layer (e.g., between nodes of the different layers), each of which may be assigned a numeric weight generated based on a pattern identified between the set of input values and the set of output values. The weight may be tuned (e.g., based on a training dataset), rendering the artificial neural network adaptive to inputs and capable of learning. Generally, the hidden layer(s) allows knowledge about the input nodes of the input layer to be shared among the output nodes of the output layer. To do so, a transformation f is applied to the input nodes through the hidden layer. The artificial neural network may also use a cost function to find an optimal solution (e.g., an optimal transformation function). The optimal solution represents the situation where no solution has a cost less than the cost of the optimal solution. In an example, the cost function includes a mean-squared error function that minimizes the average squared error between an output f (x) (e.g., a prediction, given training data input x) and a target value y (e.g., a ground truth value) over the example pairs (x, y). In some examples, a backpropagation algorithm that uses gradient descent to minimize the cost function may be used to train the artificial neural network. In this example, one or more parameters (e.g., which also may be known as "hyperparameters") may be used to administer the training process. For example, these parameters may include determining how many hidden layers of nodes to use between the input layer and the output layer, and how many nodes each layer should use. In this example, the collection of nodes and determined weights (e.g., based on training data) between interconnections of nodes between the different layers may comprise the trained model. Once the artificial neural network (i.e., prediction model) has been generated, it may be used to predict one or more events (e.g., regarding a user's present and/or future condition) upon receiving input (e.g. user data).

In a second non-limiting example, a boosted decision tree technique (e.g., XGBoost) may be used to generate a prediction model using a set of inputs (e.g., training data) that includes one or more features. Each feature may directly correspond a data point (e.g., BMI, blood pressure, etc.), or be derived from one or more data points, similar to as described earlier. This technique is also a supervised learning method and may utilize a labeled dataset with ground truth data. A pre-trained decision tree may receive a set of input features as input and then split the input data based on those features. For example, a given node in a decision tree may split (e.g., determine an outcome) based on the respective values of one or more input features input to the given node. The selection at each node of what is the next best feature to split on may be performed based at least in part on determining which features maximize information gain and/or to minimize entropy, and may be chosen as part of a (e.g., recursive) learning/training process used to generate the decision tree. The process may be repeated until a stop condition is met (e.g., the process reaches the depth of the tree, no more information gain, etc.). Terminal nodes of the decision tree may represent a class label (e.g., the user has a particular type/stage of condition) or probability (e.g., probability that a user has a condition), which may correspond to a prediction outcome. In some examples, the outcome may be a continuous variable.

Using a boosted decision tree technique, multiple weak learners (e.g., an ensemble of decision trees) may be combined into a strong classifier. In some examples, each new decision tree may be created iteratively with respect to a distribution (e.g., associated with ground truth data from a training data set), and new trees may be generated based at least in part on previous trees. On each iteration, the new tree's prediction from a data sample may be given a weight relative to its accuracy. In some examples, the ensemble output (from the multiple trees) may be a weighted sum that may be compared against the ground truth. Additionally, after each iteration, each data sample (e.g., including one or more features from the data sample) may also be given a weight based the decision tree's misclassification. In this way, the more often a data sample is misclassified, the more important the data sample (and/or individual features of the data sample) becomes. The process of training the ensemble of decision trees that collectively predict an outcome (i.e., "boosting") may also include minimizing a cost function, which, similar to above, may include a function that measures the distance between the ground truth (y) and an output f(x) (e.g., to minimize the mean-squared error).

Based at least in part on the relative weight of the output of each decision tree in an ensemble and/or the relative weights of data samples, the system may be able to determine a relative importance of features among the set of features that are represented in the ensemble of decision trees (e.g., represented by the positioning of each node within a respective decision tree and the splitting behavior assigned to the node). In some examples, the relative importance among features may represent which feature is likely to result in the most information gain among other features. The system may also be able to determine, based at least in part on the splits determined for each node in the ensemble of trees, classifier decision boundaries. A classifier decision boundary is a decision boundary that partitions an underlying vector space into two sets (e.g., user has the condition, or the user does not have the condition). In some examples, a classifier decision boundary may be determined by an ensemble of classifiers (e.g., a boosted decision tree model) based at least in part on respective values (e.g., a range of values) for one or more features of the plurality of features that are input into the model. In a simplified example, one feature may be age, and another feature may be BMI of a user. For a particular condition, the model may determine that for an age range of 60 years old or more, and a BMI range 15-17, a user would be classified as having a particular condition. In some examples, multiple classifier decision boundaries may be determined from a boosted decision tree model, which may be collectively used as input to determine a final prediction. For example, one classifier decision boundary may determine, from one set of features, that the user is likely to have a condition with a first probability. Another classifier decision boundary may determine, from another set of features, that the user is likely to have (or not have) the condition with a second probability. The first and second probabilities may be combined together to determine a final probability (e.g., prediction). In some examples, this combining process may be represented within the trained boosted decision tree model using ensemble modeling. Similar to the neural network example, one or more parameters may be used to administer the training process. For example, these parameters may include determining a maximum depth of a tree, a maximum number of leaves, a maximum number of features (e.g., from the full set of features) that may be used to build a given tree, a minimum number of samples required to make a new leaf, etc.). Once the (boosted) decision tree prediction model has been generated, it may be used to predict one or more events (e.g., regarding a user's present and/or future condition, and/or a prediction associated with the user).

While two possible examples of prediction models were mentioned above, it should be understood that any suitable prediction model may be utilized. Typically, the system will receive training data (e.g., user data received from the service organization) that is used to train the prediction model by learning characteristics (e.g., patterns and/or relationships) from the training data and thereby determining properties (e.g., weights) of the model. The system may also determine one or more parameters that may be used in training the model, whereby the parameters may be determined based on the type (e.g., structure) of model chosen (e.g., neural network, decision tree, linear regression, naive Bayes, etc.). In some examples, one or more prediction models may be chained together using an ensemble modeling to obtain better predictive performance. Additionally, in some examples, the output of one prediction model may be used as an input (e.g., as a feature) to another prediction model. For example, a first prediction model may be a neural network that predicts and/or classifies a type of skin condition. The output of the first prediction model may be used as a feature input to a second prediction model (e.g., a boosted decision tree model) that may predict a particular stage of the skin condition (e.g., injury) with a certain probability.

At block 1006, the system may generate and store the trained prediction model. The generated prediction model may include any suitable data structures utilized from block 1004 to train the prediction model, as well as learned information during the training process (e.g., a meaning assigned to a node, a position of the node within the model, a weight value for a node, etc.). In some examples, the parameters used to train the given prediction model may also be stored, for example, to be later used in updating the model. For example, the prediction model administration engine 924 may perform an audit of the prediction model, and, based on the results of the audit, determine that one or more parameters used to train the model should be adjusted (e.g., increasing the maximum number of leaves). The trained prediction model may be stored in the prediction model store 920.

At block 1008, at a later time following the generation/storage of the prediction model at block 1006, the system may receive user data for use in generating a prediction about a user. In some examples, the user data may correspond to current information about a particular user (e.g., service records for a present admission to a service facility). Similar to the training data, the user data may also include a plurality of data points that identify characteristics of the particular user. In this case, however, instead of the data being used to train a prediction model, it will be used as input into the already-trained prediction model for use in generating a prediction about the condition of the user (e.g., for the present admission). In some examples, one or more of the plurality of data points of the user data may correspond to (and/or be used to derive) features by which the prediction model was trained to make predictions. In some embodiments, the user data may include data associated with more than one user (e.g., a dependent user and/or an authorized user assigned to the dependent user).

At block 1010, the system may execute the trained prediction model on the received user data. As described earlier, the system may use the user data for the particular user to extract features that are used as input to the prediction model (e.g., to an input layer of a neural network, root node of a decision tree, etc.).

At block 1012, the system execute the trained prediction model to generate a prediction about the user. The prediction may correspond to an assessment about a present condition or potential future condition of the user. In some examples, for example, in a case where the user is a dependent user (e.g., a patient), the assessment may include data associated with a plurality of conditions of the user (e.g., multiple conditions on the body). In the case where the prediction corresponds to an assessment about a present condition, the prediction may indicate a likelihood that the user has a particular present condition. In the case where the prediction corresponds to an assessment about a potential future condition, the prediction may indicate a likelihood that the user will develop the potential future condition. As a non-limiting example, a potential future condition may correspond to the existence an illness affecting the user, a severity and/or stage of the illness, a likelihood that another related illness or condition may develop, etc. In some examples, the prediction may correspond to a probability score (e.g., between 0-1). In some examples, the prediction may correspond to a classification of a likely group to which the user belongs (e.g., Stage 1, Stage 2, Stage 3, etc.). For example, the prediction may include a plurality of probabilities that respectively correspond to a likelihood of the user's illness being at a particular stage (e.g., Stage 1=0.23, Stage 2=0.64, Stage 3=0.13). As referenced herein, depending on the context, a "prediction" may be used interchangeably with a "probability score" or "risk assessment." In some examples, the prediction may be classified based on whether or not a probability score included within the prediction matches (e.g., equals or exceeds) a predefined threshold value. For example, a user with a probability score of at least 80% may be deemed to be "High Risk." This classification based at least in part on the predefined threshold value may be built into the trained prediction model (e.g., part of the training process), or may be a separate computation that follows the prediction model outputting one or more scores. In some embodiments, the prediction may be associated with another type of user, for example, an authorized user. For example, the prediction may indicate a level of risk that the authorized user has performed a task in contravention of one or more policies. It should be understood that any suitable type of user data, prediction model, and/or prediction may be used to perform embodiments described herein.

The systems, environments, devices, components, models, and the like of FIGS. 1-10 may be used to implement a particular system as described herein with reference to later figures. In one example, a computer-based method is provided for a trained prediction model providing a prediction of whether a user (e.g., an authorized user, such as a staff member of a facility) is associated with at least one anomaly event (and/or a pattern of anomaly events). The anomaly event may correspond to an instance in which a monitored unit (e.g., a drug such as a medication, whether prescribed or not, in any form or any other substance that is monitored or otherwise controlled) has been diverted instead of being administered to a target user (e.g., a dependent user) such as a patient. A monitored unit (e.g., a monitored controlled unit or monitored dispensable unit) is diverted if some or all of the monitored unit is kept by a user other than the target user, such as staff member of a facility.

In some embodiments, a computer system that implements the above-described method for providing a prediction may receive data from one or more data sources. For example, a first data source may correspond to an automated storage and retrieval location (e.g., an automated dispensing cabinet or ADC) of a facility, which may comprise a lockable cabinet in which is stored monitored units, as described further herein. In another example, a second data source may correspond to an electronic data warehouse. For example, an electronic data warehouse may be configured to store one or more electronic records associated with users. One type of user may be a dependent user (e.g., a patient). The dependent user record may store, for example, information related to an identity of the user, one or more orders for monitored controlled units associated with the dependent user, an authorized user assigned to the dependent user, etc. Another type of user may be an authorized user (e.g., a staff member of the facility). The authorized user record may store, for example, information related to the authorized user's job title, a particular unit of the facility in which they work, their employment history, etc. It should be understood that any suitable one or more data sources may be utilized to perform embodiments described herein.

In some embodiments, the data received from one or more sources may be used to train a prediction model that outputs a prediction indicating a level of risk that a user is associated with one or more diversion events (e.g., a likely pattern of being involved with anomaly events). In some embodiments, the computer system may utilize any suitable technique(s) (e.g., one or more machine learning algorithms) to train the prediction model. For example, in some embodiments, the computer system may utilize a boosting decision tree algorithm (e.g., implementing gradient boosting) to train a prediction model that outputs a prediction. In some embodiments, the training process and/or execution process of the trained model may be similar to as described in reference to FIGS. 9 and/or 10. In some embodiments, training data that is used to train the prediction model may be determined directly or derived from the data obtained from a particular one or more data sources. For example, in some embodiments, one or more features used to train the prediction model may respectively correspond to percentile information that relates (e.g., compares) one user's (e.g., a first authorized user) use of a monitored unit to other users' use of monitored units within a particular facility. Accordingly, as described further herein, the computer system may perform one or more computations to generate features that are used as input to train the prediction model.

In some embodiments, upon training the prediction model, the computer system may subsequently utilize the trained prediction model to determine a prediction for one or more users. For example, the trained prediction model may receive data from one or more data sources. The data from each data source may include a plurality of data attributes. These attributes may be used as input to the trained prediction model, whereby the model subsequently outputs a score that corresponds to the prediction (e.g., a value between 0 and 1). In an example whereby the prediction model corresponds to a boosted decision tree, the prediction model may utilize one or more of the inputs to determine a traversal of one or more trees of an ensemble of decision trees. The output of the ensemble of decision trees may be combined (e.g., utilizing any suitable boosting technique) to generate the prediction score.

Upon generating the prediction score, the computer system may provide the prediction to a user device for presentation. For example, the user device may present the prediction score via a display to a staff member of the facility that includes the automated storage and retrieval location. In some embodiments, the user device may determine instructions (e.g., recommendations) for taking one or more actions (e.g., remedial actions) based on a level of risk that a particular user is associated with at least one anomaly event (and/or a pattern of possible anomaly events). For example, suppose that a particular prediction score (e.g., 0.90) identifies a 90% likelihood that a particular authorized user (e.g., a staff member of the facility) has diverted one or more monitored units over a period of time. The user device may provide a recommendation for further training for the particular authorized user, to ensure that subsequent actions are not in contravention of the facility's policies.

In some embodiments, the computer system may provide the prediction via a dashboard presentation via the GUI of the user device. For example, the computer system may generate a plurality of predictions, respectively, for authorized users of the facility. In some embodiments, the dashboard may be operable for ranking a level of risk of an authorized user in comparison with levels of risk of other authorized users of the facility. In some embodiments, the ranking may take into account a particular job type (e.g., role) of the facility. For example, the prediction for a particular authorized user may be determined relative to another authorized users within the same facility and/or a common role type (e.g. a similar job description).

The present disclosure provides several technical advantages over existing solutions that improve the detection of data patterns associated with anomaly events and/or users associated with anomaly events. For example, some conventional techniques may define one or more heuristics for determining whether a anomaly event occurred. For example, one heuristic may include determining that a monitored unit was removed from an automated storage and retrieval location, but that only a portion of the monitored unit was administered to a dependent user (e.g., based on an electronic record associated with the dependent user). This particular heuristic may indicate a possibility that the non-administered portion of the monitored unit was diverted. In another example, another heuristic may determine that the dependent user was discharged at a first time, but that the monitored unit was indicated as having been administered to the dependent user at a second time that follows the first time. This heuristic may also determine a likelihood that the monitored unit may have been diverted. It should be understood that there may be a plurality of heuristics respectively associated with possible scenarios for anomaly events. While these heuristics (e.g., techniques) may provide assistance in identifying anomaly events, a given heuristic may provide an assessment based on a limited set of input data (e.g., tailored for that heuristic). In some cases, this may not produce sufficiently accurate results. In some cases, maintaining multiple heuristics is also inefficient and/or produces inconsistent (or overlapping) results. In some cases, a diverter user may adjust their behavior (e.g., adapting their diversion techniques to conceal their behavior), whereby an existing heuristic may not easily updated to adapt to changing techniques used by diverters. Also, in some cases, it is difficult to utilize existing heuristics to rank and compare multiple potential diverter users. For example, a facility manager may want to identify a subset of potential diverter users (e.g., the top candidates), and channel remediation resources (e.g., training resources) to effectively address the top issues.

Embodiments of the present disclosure provide more accurate and efficient techniques for identifying potential anomaly events, as well as identifying top candidates for potential diverter users that are associated with anomaly events. For example, a prediction model may be trained based on input data from one or more sources, as described herein. One or more features may be determined (e.g., derived) from the input data, which may then be used to train the prediction model. This approach may enable the prediction model to incorporate a wider range of data than other heuristics models as training for the model. In some embodiments, the features (and/or data) used to train the prediction model may take into account comparison data (e.g., percentile data) between different users. In some embodiments, this may enable the prediction model to output a plurality of prediction score for respective users that are efficiently rankable. In some embodiments, these rankings may enable more efficient prioritization of resources to address (e.g., remediate) potential diverter users. In some embodiments, the prediction model may also be more efficiently updated to incorporate (e.g., adapt to and identify) the latest diversion behavior trends among different users. In some embodiments, the training data may be curated (e.g., downsampled) to take into account an imbalance in training samples between non-diverter samples and known diverter samples. In some embodiments, this may help to improve the precision and/or recall of the trained prediction model.

Turning to describe the system and/or various connected data sources in further detail, as introduced above, automated storage and retrieval locations provide information about monitored units in a facility setting. In some embodiments, the automated storage and retrieval locations may track what monitored units are removed from the cabinet, which target user is supposed to receive the monitored unit, how much of each monitored unit is removed, at what time each monitored unit is removed, and by whom each monitored unit is removed. This information is stored into archive files that are periodically output by the automated storage and retrieval location (e.g., every 24-48 hours). The system accesses these archive files and compares their contents with data accessed from a record storage such as an electronic record relating to what happened with the monitored units. The storage record data may indicate when, how much, by whom, and to which target user each monitored unit was administered. The system can track whether all of a monitored unit was administered (e.g., two units were removed and one unit was documented as administered, with no documented wastage or return), whether the monitored unit was administered within an appropriate time window (e.g., 30 minutes), whether the target user's pain scale was recorded before and after administration of the monitored unit, a difference in the target user's pain scale before and after administration of the monitored unit, and whether the monitored unit was removed after the target user was discharged.

Another example supplements the system for detecting instances in which a monitored unit has been diverted instead of being administered to a target user. The system may use signals from scheduling applications and/or timekeeping applications to determine which authorized users were working at the time of an anomaly event. Alternatively or in addition, location data of user devices may be used to track the locations of the authorized users. The total hours worked and the dates and times at which an authorized user was scheduled to work may be used to determine whether the authorized user was scheduled to work when the authorized user withdrew the monitored unit from the automated storage and retrieval location. This information may also be used to compare the authorized user with the authorized user's peers, because if the authorized user works more hours than the authorized user's peers, the authorized user may be more likely to divert the monitored unit. Other systems, such as geolocation systems, may be used to track the location of a target user. For example, this information can be used to determine whether the target user was in the facility when the monitored unit was removed from the automated storage and retrieval location.

Another example supplements the system for detecting instances in which a monitored unit has been diverted instead of being administered to a target user. The method may use near real-time data from the record storage along with near real-time data from the automated storage and retrieval location. This enables identification of poor monitored unit practices (e.g., taking too long to document waste of monitored units) and catching of diverters before they leave the facility.

Another example supplements the system for detecting instances in which a monitored unit has been diverted instead of being administered to a target user. The system may utilize data associated with an authorized user. For example, the data may include data attributes associated with a particular facility (and/or department within the facility) in which the authorized user works, a job title, an employment history of the authorized user, demographics of the authorized user, etc. In some embodiments, the historical data may previous anomaly events associated with the authorized user. The historical data may also indicate any suitable data associated with the use by the authorized user of one or more monitored units, a time that a monitored unit was withdrawn from an automated storage and retrieval location by the authorized user, etc. In some embodiments, a type of use of the monitored unit may include an administration of the monitored unit, discarding the monitored unit, or returning the monitored unit to the automated storage and retrieval location.

Another example supplements the system for detecting instances in which a monitored unit has been diverted instead of being administered to a target user. The system may use a signal from a monitored unit pump to indicate the time and quantity of a monitored unit that was administered to a target user. The signal may include the settings that were entered into the pump before the monitored unit was administered. The signal may be used to corroborate or replace the record storage data.

Another example supplements the computer-based method for detecting instances in which a monitored unit has been diverted instead of being administered to a target user. The method may use a signal that includes controlled-substance information (e.g., CIISafe data). For each safe, the signal may indicate when a quantity of a monitored unit was received by and removed from the safe. This would allow tracking of monitored units from the safes, to the automated storage and retrieval location, to the target users, and any interruptions along the way. For example, it may be determined if a monitored unit was removed from a safe but did not reach an automated storage and retrieval location.

Another example supplements the computer-based method for detecting instances in which a monitored unit has been diverted instead of being administered to a target user. The method may determine whether the monitored unit was properly administered according to the parameters of a request. For example, it may be determined if the administration complied with the dose (such as 1 mg), the frequency (such as every 4 hours), and the pain scale (such as between 1 and 3).

Figure 11:
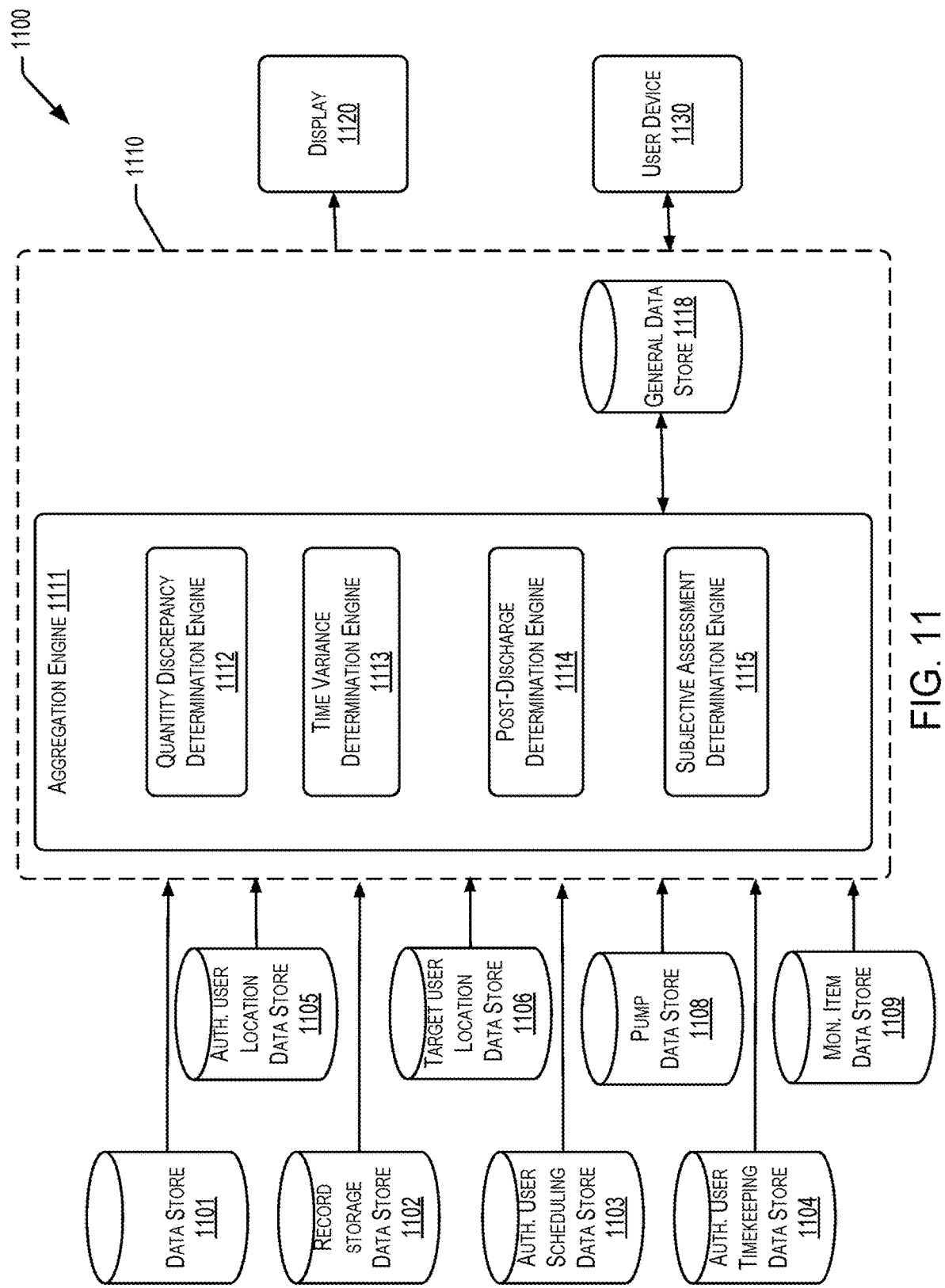
FIG. 11 is an example schematic architecture illustrating a system in which techniques relating to aggregating data from disparate sources for anomaly event prediction may be implemented, according to at least one example.

Referring now to FIG. 11, a block diagram of an example of a system 1100 is shown. The system 1100 includes a transformative processing engine 1110. The transformative processing engine 1110 is an example of the transformative processing engine 108 discussed with reference to FIG. 1. The transformative processing engine 1110 includes an aggregation engine 1111 and a general data store 1118. The aggregation engine 1111 is an example of the aggregation engine 218 discussed with reference to FIG. 2.

Generally the aggregation engine 1111 is configured to collect data from various sources and to perform one or more operations on the collected data. For example, the aggregation engine 1111 may collect facility data from an automated storage and retrieval location data store 1101, record storage data from an record storage data store 1102, authorized user scheduling data from an authorized user scheduling data store 1103, authorized user timekeeping data from an authorized user timekeeping data store 1104, authorized user location data from an authorized user location data store 1105, target user location data from a target user location data store 1106, pump data from a pump data store 1108, and monitored item data from a monitored item data store 1109. In some embodiments, the prediction model management engine 902 of FIG. 902 may receive data from one or more of the various data sources of FIG. 11 and/or the transformative processing engine 1110 of FIG. 11, which may subsequently be used to train a prediction model, described herein.

The automated storage and retrieval location data may include data from one automated storage and retrieval location or a plurality of automated storage and retrieval locations in a facility. For each automated storage and retrieval location, the automated storage and retrieval location data may include information about a plurality of monitored units. For each monitored unit that is withdrawn from the automated storage and retrieval location, the automated storage and retrieval location data may indicate which target user is supposed to receive the monitored unit, how much (e.g., an amount) of the monitored unit is removed, at what time the monitored unit is removed, and by whom the monitored unit is removed. After the monitored unit has been removed, the automated storage and retrieval location may also track whether the monitored unit is administered to the target user, wasted (i.e., discarded), and/or returned. This information is provided by authorized users who enter the information into the automated storage and retrieval location and, if appropriate, return part or all of the monitored unit to a separate drawer in the automated storage and retrieval location. In some embodiments, the automated storage and retrieval location data may indicate whether the monitored unit is a controlled substance (e.g., a drug that is regulated by a law) or a non-controlled substance. In some embodiments, the automated storage and retrieval location data may include information about whether a monitored unit was removed and/or administered with or without an associated order. In some embodiments, the automated storage and retrieval location data may indicate whether the monitored unit was returned to the same automated storage and retrieval location from which it was originally removed, or whether there is a mismatch (e.g., returned to another automated storage and retrieval location). In some embodiments, the automated storage and retrieval location data may include information associated with an amount of the monitored unit involved for any suitable usage step (e.g., removal from the automated storage and retrieval location, administration of the portion of the monitored unit (e.g., before and/or after a pain assessment is administered), returning the monitored unit to the automated storage and retrieval location, etc.). In some embodiments, pump data (e.g., from a medication pump) may be used alternatively and/or as a supplement to confirm an amount of the monitored unit that is administered. The amount of the monitored unit involved may be correlated with a particular time event. These data points may be subsequently used as data attributes that may be used to train a prediction model (and/or execute a trained prediction model).

The record storage data may include a summary of electronic record information for each of a plurality of target users at the facility. For each target user, the record storage data may include the parameters of at least one order for the target user, such as the dose, frequency, and pain scale at which each monitored unit should be administered. For each target user, the record storage data may indicate when, how much, and by whom each monitored unit was administered to the target user. For example, the record storage data may indicate data about a particular authorized user who is assigned to a target (e.g., dependent) user for administering the monitored unit. The record storage data may also indicate when the target user was admitted and discharged, along with any tests, procedures, etc. that the target user had while at the facility. In addition, the record storage data may include pain assessments from the target user at various times. This information is provided by authorized users who enter the information into the record storage. For example, the record storage data may be received from a data warehouse, streamed from a user device (e.g., a first authorized user's computer or mobile device), or streamed from a device or equipment (e.g., a monitored unit dispensing unit). In some embodiments, the record storage data may indicate whether there are any discrepancies with respect to a usage of the monitored unit. For example, the record storage data may indicate whether the time in which the monitored unit was administered differs from another time the administration of the monitored unit was recorded in the system by more than a threshold amount of time (e.g., 5 minutes). In some embodiments, any suitable time measurements may be included within record storage data that are associated with the usage (e.g., dispensing, administration, returning, and/or discarding) of a monitored unit. It should be understood that the record storage data (and/or other suitable data described herein) may include historical data over one or more transactions involving an authorized user and/or dependent user. Accordingly, as described further herein, statistical data may be determined based in part on the historical data tracking. This statistical data may be further utilized to compute derivative data, for example, comparing different authorized users by computing percentile data with respect to one or more statistical values.

The authorized user scheduling data may include a list of authorized users who are scheduled to work at a facility over the course of a time period. The authorized user scheduling data may also include the start time and the end time of each authorized user's shift, along with the start time and the end time of any scheduled breaks.

The authorized user timekeeping data may include records of time card punches made by authorized users at various punch clocks within the facility over the course of a time period. The punch clocks may be manual or electronic, and the punch clock data may indicate which punch clock was used for each time card punch, including the location of the punch clock.

The authorized user location data may include records of locations of authorized users within the facility over the course of a time period. For example, the authorized user location data may include records of when an authorized user entered and/or left an area, such as a target user's room or a room in which an automated storage and retrieval location is located, based on wireless transmissions from an application on the authorized user's smartphone, badge, etc. Any suitable wireless communication technology may be used, such as WiMAX, WiFi, radio, cellular networks, etc.

The target user location data may include records of locations of target users within the facility over the course of a time period. For example, the target user location data may include records of when a target user entered and/or left an area, such as the target user's room or a room in which an automated storage and retrieval location is located, based on scans from the target user's identification bracelet.

The pump data may include records from monitored unit pumps within the facility. For each pump, the pump data may include the time that a monitored unit was administered to a target user, the quantity of the monitored unit that was administered, the authorized user who administered the monitored unit, and/or the identity of the target user. Some or all of this information may be entered into the settings of the monitored unit pump before the monitored unit is administered.

The monitored item data may include records from safes within the facility that store monitored units, such as controlled substance safes. For each safe, the monitored item data may include information about a plurality of monitored units. For each monitored unit, the monitored item data may indicate how much of the monitored unit is received by the safe, when the monitored unit is received by the safe, how much of the monitored unit is removed from the safe, and/or when the monitored unit is removed from the safe.

The automated storage and retrieval location data, record storage data, authorized user scheduling data, authorized user timekeeping data, authorized user location data, target user location data, pump data, and/or monitored item data may be updated periodically, such as every minute, every thirty minutes, every hour, every two hours, every four hours, every day, every week, or every month. For example, the automated storage and retrieval location data may be stored into archive files that are periodically output by the automated storage and retrieval locations, such as every 24-48 hours. Alternatively, the automated storage and retrieval location data may be updated and accessed in near real-time, such as every 1-5 minutes. Further, the automated storage and retrieval location data, record storage data, authorized user scheduling data, authorized user timekeeping data, authorized user location data, target user location data, pump data, and/or monitored item data may be sent to the transformative processing engine 1110 periodically, such as every minute, every thirty minutes, every hour, every two hours, every four hours, every day, every week, or every month. The aggregation engine 1111 may aggregate the data periodically at any suitable interval. In some embodiments, any one or more of the data types may include a plurality of data attributes associated with the respective data type. As described further herein, these attributes may be used to train a prediction model that is used to output a prediction score. For example, attributes may be used to determine features that are used to train a prediction model. In some cases, a feature may directly correspond to an attribute (e.g., a dose amount, an amount of the monitored unit that is wasted, etc.). In some embodiments, a feature may be derived (e.g., computed) from the one or more attributes. For example, a feature may correspond to statistical information that is computed from one or more attributes and/or in comparison with data associated with one or more users. For example, an example feature may correspond to an average number of pain reassessments missing per month, for a given time period (e.g., six months). Another example feature may correspond to a percentile value of a user (e.g., compared to other users) for an average monthly number of controlled inventory transactions over a given time period. It should be understood that any suitable number and/or type of features may be determined from one or more sets of data attributes. It should be also be understood that the data types (e.g., automated storage and retrieval location data, record storage data, etc.) may be received from any suitable one or more data sources (e.g., an automated storage and retrieval location, a data server connected to an automated storage and retrieval location, an electronic data warehouse, etc.).

The aggregation engine 1111 may aggregate some or all of the data. The aggregation engine 1111 may include various engines for aggregating the data, such as a quantity discrepancy determination engine 1112, a time variance determination engine 1113, a post-discharge determination engine 1114, and a subject assessment determination engine 1115 (e.g., to determine and/or compare pain assessments). These engines will be described in further detail below. It should be understood that these engines are representative of various types of data that may be aggregated, for example, to be used in training a prediction model. After aggregating the data, the aggregation engine 1111 may send the results to a general data store 1118, which is configured to store the results. Further, the transformative processing engine 1110 may output the results to a display 1120 and/or a user device 1130. As described herein, the transformative processing engine 1110 may also (and/or alternatively) transmit the data to the prediction model management engine 902, for example, from the general data store 1118. These data may be used to train a prediction model and/or as input to a trained prediction model, for generating a prediction score.

Turning to the quantity discrepancy determination engine 1112 in further detail, the engine 1112 may determine any suitable quantity (e.g., dosage) discrepancy related to the usage (e.g., withdrawal, administration, discarding, and/or returning) of a monitored unit. For example, the engine 1112 may determine the quantity of the monitored unit that was withdrawn from the automated storage and retrieval location for the target user based on automated storage and retrieval location data from the automated storage and retrieval location data store 1101. For example, the quantity may be provided in units of mass (such as mg), volume (such as mL), or number of dosage forms (such as number of capsules). The quantity of the monitored unit that was administered to the target user may then be extracted from the record storage data from the record storage data store 1102. Alternatively or in addition, the quantity of the monitored unit that was administered to the target user may be extracted from the pump data from the pump data store 1108. Based on the extracted information, it may be determined whether the administered quantity of the monitored unit was smaller than the withdrawn quantity of the monitored unit. For example, if 10 mg of the monitored unit was withdrawn and 10 mg of the monitored unit was administered, then it may be determined that none of the monitored unit was diverted. On the other hand, if 10 mg of the monitored unit was withdrawn and 5 mg of the monitored unit was administered, then it may be determined that 5 mg of the monitored unit may have been wasted or diverted. In this case, similar to other extracted data described herein, this extracted data may be stored via one or more data attributes that are subsequently used to train a prediction model. In another example, the engine 1112 may receive from the monitored item data store 1109 data about a monitored unit that was removed from a safe. The data may indicate if the monitored unit was sent to an automated storage and retrieval location or an area of the facility other than the automated storage and retrieval location. In some embodiments, the quantity of the monitored unit that was removed from the safe may be extracted from the data, and the quantity of the monitored unit that was received by the automated storage and retrieval location may also be extracted. A difference between the two quantities may be determined and stored.

Turning to the time variance determination engine 1113 in further detail, the engine 1113 may determine any suitable time variances associated with usage of a monitored unit. For example, the engine 1113 may extract from the automated storage and retrieval location data the time that the monitored unit that was withdrawn from the automated storage and retrieval location for the target user. The time that the monitored unit that was administered to the target user may also be extracted from the record storage data. Based on the extracted information, it may be determined whether the monitored unit was administered more than a predetermined time after the monitored unit was withdrawn. In another example, the engine 1113 may determine a time variance between a time the monitored unit was administered, and another time the administration of the monitored unit was recorded.

Turning to the post-discharge determination engine 1114 in further detail, the engine 1114 may determine data related to usage of a monitored unit post-discharge of a user. For example, the engine 1114 may extract from the automated storage and retrieval location data the time that the monitored unit that was withdrawn from the automated storage and retrieval location for the target user. The time that the monitored unit that was administered to the target user may then be extracted from the record storage data (e.g., from the record storage data store 1102). In addition, data about the location of the target user in the facility as a function of time may be received. For example, the data may include the target user location data from the target user location data store 1106. Based on the extracted information, it may be determined whether the monitored unit was withdrawn or administered after the target user was discharged.

Turning to the subjective assessment determination engine 1115 in further detail, the engine 1115 may determine subjective assessments associated with a target user. In some embodiments, the assessments may be respectively associated with a particular time. For example, a first pain scale may be determined for the target user before the monitored unit was administered. The record storage data from the record storage data store 1102 may indicate the time that the monitored unit was administered and may include any pain scales that were obtained from the target user, along with the times at which the pain scales were obtained. In some embodiments, the engine 1115 may determine if any pain assessments were not recorded before or after administration of a monitored unit. In some embodiments, the engine 1115 may determine changes in the subjective assessments (e.g., the pain scale) of a given user before and after administration of the monitored unit.

Figure 12:
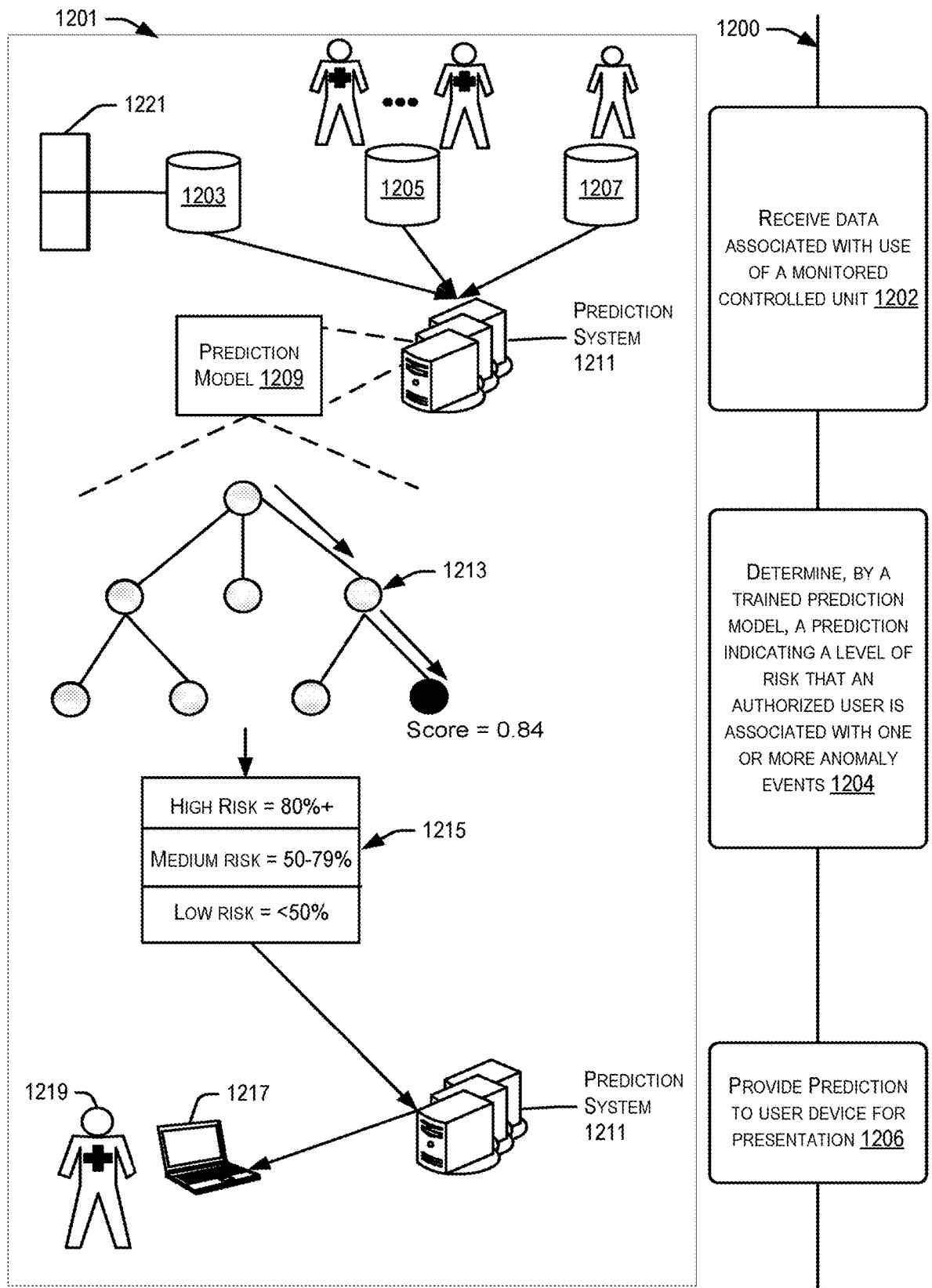
FIG. 12 is an example diagram illustrating a process for providing a prediction that a user is associated with one or more anomaly events, according to at least one example.

FIG. 12 illustrates a simplified block diagram 1201 depicting an example process 1200, in accordance with at least one example. The process 1200 is an example process for providing a prediction that a user is associated with one or more anomaly events. The diagram 1201 depicts example states that correspond to the blocks of the process 1200. The diagram 1201 includes an automated storage and retrieval location (automated storage and retrieval location) 1221 that is connected to a first data store 1203, a second data store 1205, and a third data store 1207. Each of the data stores may feed into the prediction system 1211, which may utilize data from the stores to determine a prediction score, as described herein. In some embodiments, the automated storage and retrieval location 1221 itself may include a data store and/or may be directly connected to the prediction system 1211.

In some embodiments, the data stores may respectively correspond to data sources (e.g., a first data source, a second data source, and a third data source) that feed into a prediction system 1211. It should be understood that any one or more of the data stores of FIG. 12 may correspond to (e.g., include data from) any suitable one or more data stores described herein (e.g., data stores of FIG. 11). For example, the first data store 1203 may correspond to the automated storage and retrieval location data store 1101 of FIG. 11, the pump data store 1108, the monitored item data store 1109, etc. The second data store 1205 may include data associated with one or more authorized users, for example, including data from the authorized user scheduling data store 1103, the authorized user timekeeping data store 1104, the authorized user location data store 1105, etc. The third data store 1207 may include data associated with user records (e.g., target user records), for example, included within the record storage data store 1102, the target user location data store 1106, etc.

The prediction system 1211 may include, among other things, a prediction model management engine 902 of FIG. 9. The prediction system 1211 may also be connected to (and/or include) a transformative processing engine 1110, which may collate data received from the one or more data sources. The prediction system 1211 may include a trained prediction model 1209 that is trained to output one or more prediction scores to a user device 1217, whereby the prediction scores (and/or recommendations for taking action based on the scores) may be presented by the user device 1217 to a user 1219.

The process begins at block 1202, whereby the prediction system 1211 receives data associated with use of a monitored controlled unit. For example, the data may be received from one or more of the data stores (e.g., data store 1203, 1205, and/or 1207). The data may include a plurality of data attributes. Some non-limiting examples of data attributes may include, an amount of a monitored unit withdrawn from the automated storage and retrieval location 1221, an amount of the monitored unit administered to a particular target (e.g., dependent) user, an identity of an authorized user assigned to administer to the patient the monitored unit associated with a particular order, an initial pain score prior to administration of the monitored unit, a pain reassessment score, a type of the monitored unit, etc.

In some embodiments, the prediction system 1211 may receive data on any suitable cadence and/or may include an aggregation of data. For example, in some embodiments, data may be received every several minutes, daily, or weekly. In some embodiments, the data may be associated with a plurality of users. For example, data that is received daily may include a list of orders for a particular facility for a given day. Each order may be associated with usage of one or more monitored units, and/or may be associated with a particular authorized user. Accordingly, the aggregate data may indicate a plurality of authorized users. The authorized users may respectively be assigned to administer a request. In some cases, the list of authorized users may include authorized users who were on shift at the time the monitored unit was withdrawn from an automated storage and retrieval location. In some embodiments, an authorized user may have dispensed at least one monitored unit within a given month. In some embodiments, the prediction system 1211 may receive and store historical data over a period of time (e.g., six months, a year), which may be used as input to the prediction model 1209.

In some embodiments, the prediction system 1211 may determine one or more features from the data attributes received from the one or more data sources. In some embodiments, a feature may directly correspond to a particular data attribute. In some embodiments, a feature may be derived (e.g., computed) from one or more data attributes. For example, in some embodiments, a feature correspond to a statistic that measures historical data over time. (e.g., a number of removals of a monitored unit by a particular user over a period of a month). In some embodiments, a feature may correspond to a statistic that compares a particular user with one or more other users (e.g., a percentile compared to other users within the same facility and/or the same job title for an average monthly number of monitored unit transactions over a particular time period).

In some embodiments, any suitable number of features may be determined, which may be used as input to the trained prediction model 1209. For example, as depicted in Table 1 below, twenty-four features are used as inputs to the trained prediction model 1209. It should be understood that the features included in Table 1 below are representative of example features that may be used to train a prediction model. Any suitable number and/or type of features (e.g., determined from the data attributes of the one or more data stores) may be utilized as input a trained prediction model. In some embodiments, as described further herein, the features may also be used to train a prediction model.

TABLE 1

| Feature # | Feature | Definition |
|---|---|---|
| 1 | Percent Controlled (Dispensed) | Total number of controlled dispenses divided by total number of dispensed transactions over the time period |
| 2 | # Dose Variances (Controlled) | Average number of dose variances for controlled monitored units (e.g., medications) per month over the time period |
| 3 | # of Pain Reassessments Missing | Average number of pain reassessments missing per month over the time period |
| 4 | # of Wastes (Controlled) | Average number of wastes of controlled meds per month over the time period |
| 5 | Average Admin-Filed Elapsed Minutes for Scheduled Controlled Meds | Average minutes elapsed between administering and filing timestamps for controlled meds over the time period |
| 6 | Avg. Initial Pain Score | Average initial pain scores over the time period |
| 7 | Avg. Pain Reassessment Score | Average pain reassessment scores over the time period |
| 8 | Percent Overrides (Non-Controlled) | Number of overrides on non-controlled meds divided by total number of dispenses over the time period |
| 9 | Percent Wastes (Controlled) (out of total dispensed transactions) | Number of controlled wastes divided by total number of dispenses transactions over the time period |
| 10 | Rank of # Inventories (Controlled) | Percentile compared to other users with the same facility/Role (e.g., job) type for average monthly number of controlled inventory transactions over the time period |
| 11 | Rank of # Machine Mismatches (Controlled) | Percentile compared to other users with the same Facility/Role type for average monthly number of machine mismatches on controlled meds over the time period |
| 12 | Rank of # Z orders with Admin-Filed Time Discrepancy (Controlled) | Percentile compared to other users with the same Facility/Role type for average monthly number of Z orders with more than 5 minutes difference between admin and filing timestamps on controlled meds over the time period |
| 13 | Rank of Avg Dispense-Admin Elapsed Minutes (Controlled) | Percentile compared to other users with the same Facility/Role type for average minutes elapsed between dispense and administration on controlled meds over the time period |

TABLE 1-continued

| Feature # | Feature | Definition |
|---|---|---|
| 14 | Rank of Avg. Dispense-Filed elapsed time (Controlled) | Percentile compared to other users with the same Facility/Role type for average minutes elapsed between dispense and filing on controlled meds over the time period |
| 15 | Rank of Avg. Dispense-Filed Elapsed Time (Non-Controlled) | Percentile compared to other users with the same Facility/Role type for average minutes elapsed between dispense and filing for non-controlled meds over the time period |
| 16 | Rank of Dose Variances (Controlled) | Percentile compared to other users with the same Facility/Role type for average monthly number of dose variances on controlled meds over the time period |
| 17 | Rank of Full Dose Wastes (Non-Controlled) | Percentile compared to other users with the same Facility/Role type for average monthly number of full dose wastes on non-controlled drugs over the time period |
| 18 | Rank of Percent Controlled (Dispensed) | Percentile compared to other users with the same Facility/Role type for percent controlled (number controlled dispenses divided by total dispenses) over the time period |
| 19 | Rank of Percent Machine Mismatch (Non-Controlled) | Percentile compared to other users with the same Facility/Role type for percent machine mismatch (number of machine mismatch divided by dispensed transactions) on non-controlled drugs over the time period |
| 20 | Rank of Percent Pain Reassessment Missing | Percentile compared to other users with the same Facility/Role type for percent pain reassessment missing (number pain reassessments missing divided by total number of administered transactions) over the time period |
| 21 | Rank of Percent Pantoprazole | Percentile compared to other users with the same Facility/Role type for percent pantoprazole (number of pantoprazole dispenses divided by total number of dispenses) over the time period |
| 22 | Rank of Post Discharge Dispenses | Percentile compared to other users with the same Facility/Role type for average number of post discharge transactions over the time period |
| 23 | Rank of Total # Transactions | Percentile compared to other users with the same Facility/Role type for total number of transactions |
| 24 | Total # Dispensed Controlled | Percentile compared to other users with the same Facility/Role type for average number of controlled transactions dispensed per month over the time period |

At block 1204, the trained prediction model 1209 of the prediction system 1211 may determine a prediction score that indicates a level of risk that an authorized user is associated with one or more anomaly events. In some embodiments, the prediction score may be associated with a likelihood of a pattern of anomaly events. Using diagram 1201 for further illustration, suppose that the prediction model 1209 utilizes a gradient boosting machine learning technique via an ensemble of weak prediction models (e.g., decision trees). In this example, the prediction model 1209 may be trained similar to as described in reference to FIG. 10 and or FIG. 14, described further herein. Although diagram 1201 only depicts one example decision tree 1213, it should be understood that decision tree 1213 may be a representative tree of an ensemble of decision trees. The output of the respective decision trees may be merged together to produce the prediction score. In the example of diagram 1201, the prediction score for a particular user (e.g., an authorized user) is 0.84 (e.g., 84%). In some embodiments, the prediction score may correspond to a likelihood that the particular user is associated with at least one anomaly event. For example, the particular user may be likely to have directly diverted a monitored unit from a target (e.g., dependent user), and/or have assisted another user in performing the diversion. In some embodiments, the score may be associated with a particular pattern of diversion. In some embodiments, the prediction score may be classified into a particular category of a plurality of possible risk categories 1215. For example, in the example of diagram 1201, the particular authorized user may be categorized as being "High Risk," since their prediction score is greater than 80%. In some embodiments, the risk classification may be determined relative to other similar users (e.g., relative to other authorized users within the same facility that employs the authorized user and/or having a common role type (e.g., a same job description). It should be understood that any suitable classification and/or ranking technique may be utilized to perform embodiments herein. In some embodiments, by determining a risk ranking profile for a given user that is relative to other users, the prediction system 1211 may enable more efficient prioritization of remediation resources to address users who are potential diverters.

At block 1206, the prediction system 1211 may provide the prediction score to the user device 1217 for presentation to the user 1219. In one example, the prediction score may be displayed via a graphical user interface (GUI) of the user device 1217. The user device 1217 may correspond to any suitable user device (e.g., a desktop computer, mobile device, tablet, etc.) that is communicatively connected to a display unit. The GUI may correspond to a dashboard that is operable for ranking the level of risk of the user (e.g., the authorized user) associated with the prediction score in comparison with levels of risk of other authorized users of the facility. Accordingly, as described further in reference to FIG. 14, the dashboard may display a list of prediction scores, respectively, for different authorized users. In some embodiments, any suitable data may be provided for presentation to the user device 1217. This may include, for example, statistical information associated with user behavior (e.g., a facility at which the user is employed, hours worked, a quantity of waste over a particular time period, etc.).

Figure 13:
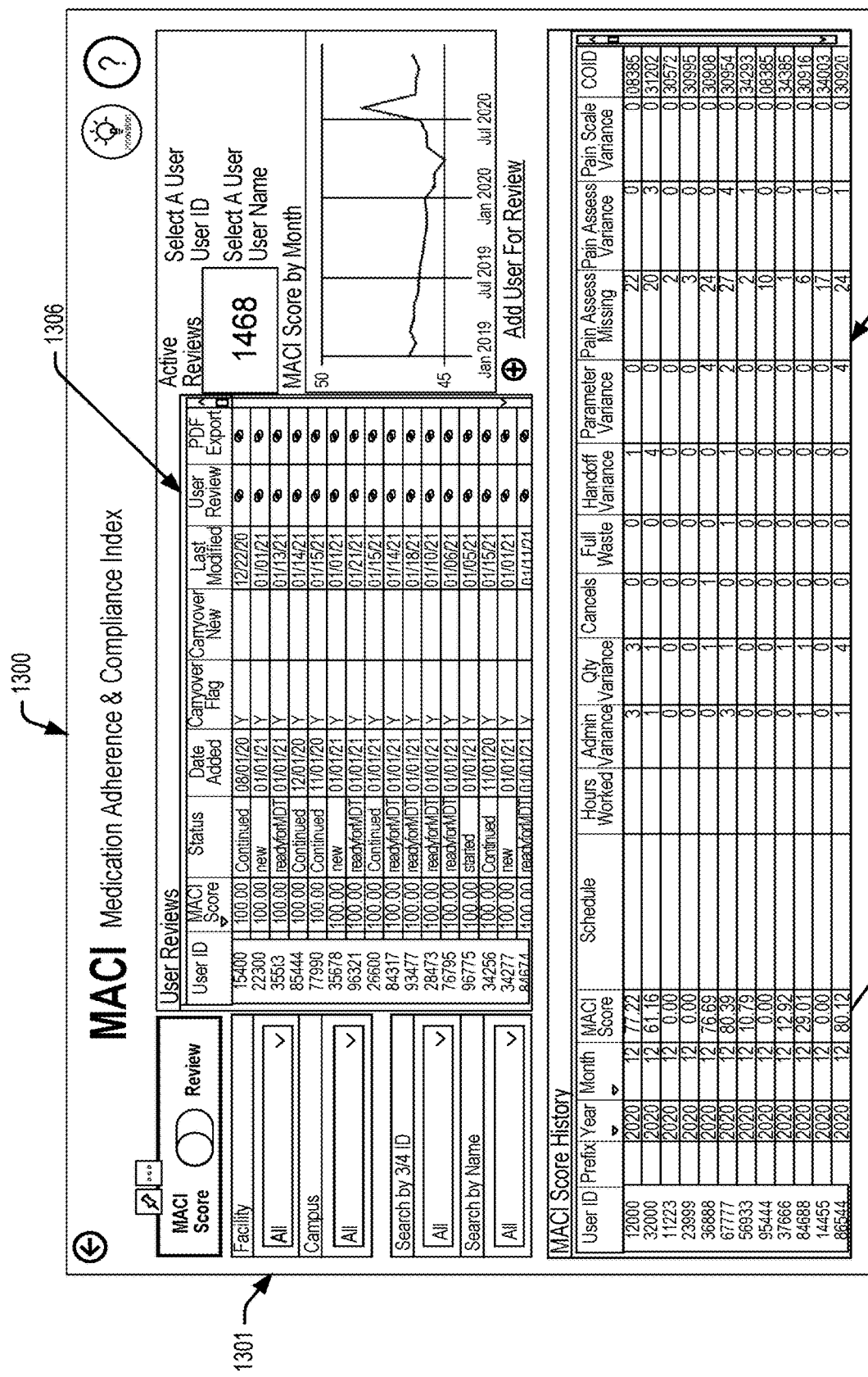
FIG. 13 is an example diagram illustrating a graphical user interface (GUI) for providing a prediction that a user is associated with one or more anomaly events, according to at least one example.

FIG. 13 is an example diagram illustrating a graphical user interface (GUI) of a display of a user device. In some examples, the user device may be similar to user device 1217 of FIG. 12. In some embodiments, the GUI may correspond to a dashboard 1300 display of an application executing on the user device. In some embodiments, the dashboard 1300 may be provided to the user device 1217 at block 1206 of FIG. 13. The application may enable a user to visualize a distribution (e.g., an ordered list) of users that are ranking according to their respective prediction levels.

For example, as depicted in FIG. 13, the dashboard 1300 may be present a ranked list of prediction scores for respective authorized users. In this example (e.g., a medical context), the prediction score may be referred to as a "Medication Adherence and Compliance Index" score (a "MACI" score). On the left side of the dashboard 1300, one or more filters 1301 are displayed. For example, as depicted in the dashboard 1300, one or more filters 1301 may enable a user to filter by Facility or Campus. The user may be able to also search by a user identifier and/or name (e.g., staff members of the particular selected Facility). In some embodiments, a list of prediction (e.g., MACI) scores may be generated per facility. As described herein, in some embodiments, the prediction scores for a given facility may be generated relative to one another (e.g., ranked relative to other users within the same facility). In some embodiments, the authorized users may be ranked according to a common role type (e.g., the same job position).

Turning to the dashboard 1300 in further detail, the dashboard 1300 may include prediction score history and associated data for a plurality of users. For example, table 1304 may include a plurality of columns. The plurality of columns may include, among other columns, column 1302 ("MACI" score) that corresponds to assessment score history for a plurality of users (e.g., authorized users). Other columns may include, by way of illustration, "User ID," "Schedule," "Hours Worked," "Administration Variance," "Quantity Variance," "Cancels", "Full Waste," "Handoff Variance," "Parameter Variance," "Pain Assessments Missing," "Pain Assessments Variance," "Pain Scale Variance," "Facility ID," etc. In one example, the "Administration Variance" may indicate a number of times that orders were not administered in accordance with the order by a particular user. In another example, the "Quantity Variance" may indicate an aggregate amount of the monitored unit that varied from the amount in the original order(s). In yet another example, the "Full Waste" may indicate the total amount wasted over a given time period (e.g., a month). It should be understood that any suitable information may be displayed within the table 1304.

In some embodiments, the table 1304 may enable rows to be sorted in a ranking order. For example, the MACI scores of column 1302 may be sorted from highest to lowest. In this way, a user of the dashboard 1300 may efficiently determine which users are the highest likely candidates for further review (e.g., to determine if a particular user is associated with one or more anomaly events).

In some embodiments, the dashboard 1300 may also include recommendations for remediating a user who may be a likely diverter. For example, the prediction model 1209 may output a recommendation for following up with the user with particular remediation steps, based in part on the data input to the prediction model 1208. For example, the prediction model may determine, based on the score and/or other input features to the model, that the user would benefit from additional training on procedures regarding usage of monitored units (and/or other procedures) within the facility (e.g., administration of a monitored unit to a dependent user, recording the administration of the monitored unit, handling waste, clocking out promptly, etc.). In some embodiments, for example, if the system determines a high likelihood that a user has a pattern of anomaly events, the system may determine that other remediation measures may be useful.

In some embodiments, the dashboard 1300 may also present a table 1306 that indicates a current status of one or more users with respect to ongoing remediation steps and/or recommendations for action to be taken. For example, the table 1306 may indicate whether remediation steps are already being taken or whether it is a new case. In some embodiments, the dashboard 1300 may also indicate a total number of users that are being actively reviewed (e.g., with a MACI score greater than a particular threshold value, such as 90%). The dashboard 1300 may also indicate (e.g., graphically or tabular) a trend of MACI score over time for a particular user and/or a plurality of users of a facility. In some embodiments, the table 1306 may highlight a subset of users from table 1304 which are top candidates for being reviewed with higher priority.

Figure 14:
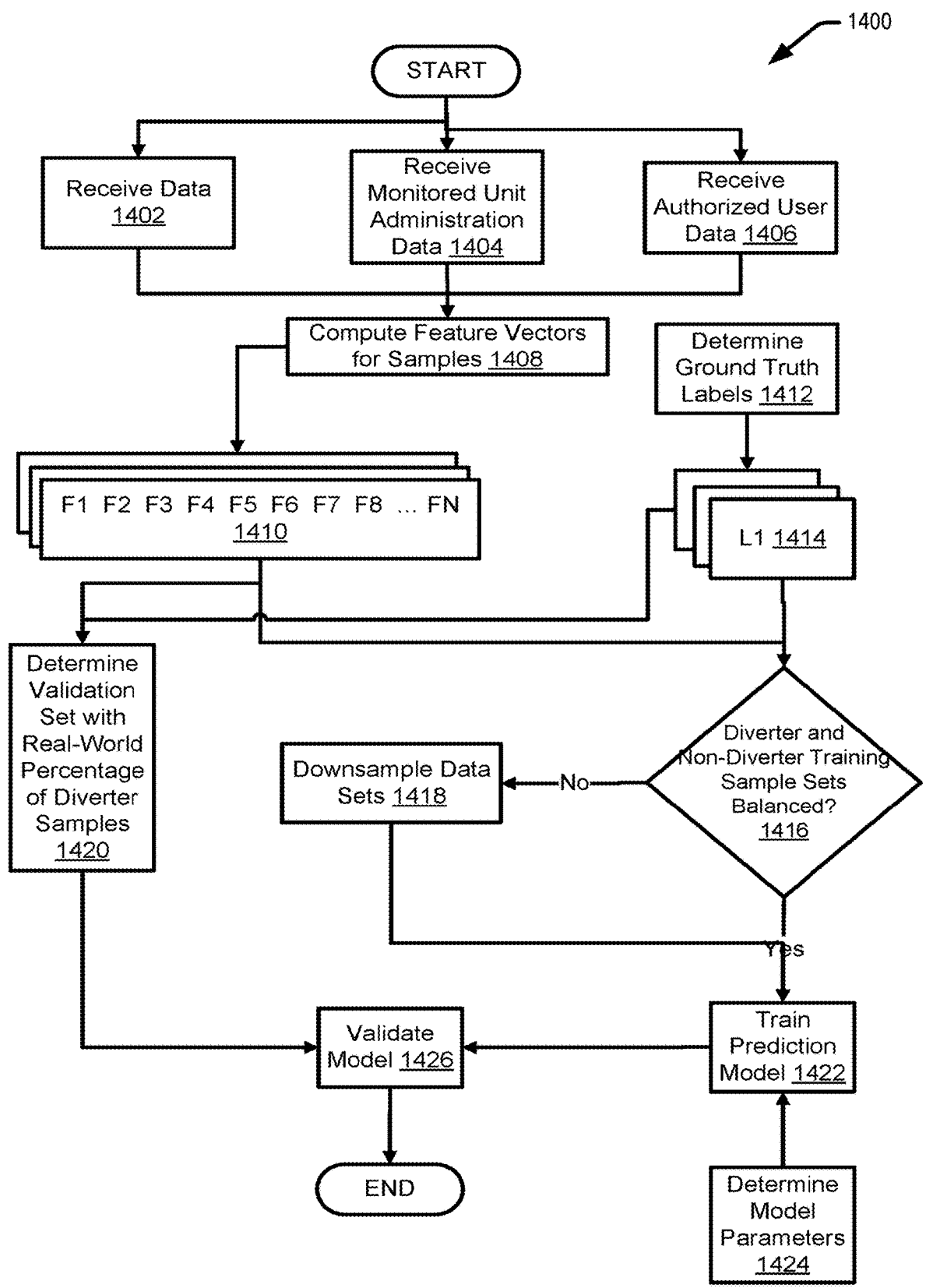
FIG. 14 is an example flow diagram illustrating a flow for training a prediction model to generate a prediction that a user is associated with one or more anomaly events, according to at least one example.

FIG. 14 is an example flow diagram illustrating a flow for training a prediction model to generate a prediction that a user is associated with one or more anomaly events, according to at least one example. In flow 1400 of FIG. 14, the process may start by a computer system (e.g., prediction system 1211 of FIG. 12) receiving data. In the example of flow 1400, the computer system may receive automated storage and retrieval location data 1402, monitored unit administration data 1404, and authorized user data 1406. In some embodiments, each of these types of data may come from respectively different data sources, the same data source, or any suitable combination of data sources (e.g., one or more of the data stores of FIG. 9). In some embodiments, the respective data may include a plurality of attributes.

For example, the automated storage and retrieval location data attributes (e.g., first data attributes) may identify an identity of a dependent user to receive a monitored unit that is withdrawn from the automated storage and retrieval location, a quantity of the monitored unit that was removed, a time that the monitored unit was removed, and identity of the user (e.g., the authorized user) who removed the unit, an identification of the use of the monitored unit after removal, etc. It should be understood that the automated storage and retrieval location data may include a plurality of samples of data associated with one or more monitored units (e.g., a type of use involving the respective monitored unit).

In another example, the monitored unit administration data for a particular order may also include a plurality of attributes (e.g., second data attributes) that identify, for example, one or more of a dosage associated with the order, a frequency associated with the order (e.g., how often the order may be issued for a dependent user), a scale (e.g., a pain scale) associated with the order, an identity of an authorized user associated with the order, an identity of the dependent user, a time at which the monitored unit was administered to the dependent user, and/or a quantity of the monitored controlled unit administered to the dependent user. In yet another example, the authorized user data may include a third plurality of attributes, for example, indicating a facility that the authorized user is employed, a role type, a unit (e.g., department) of the facility in which the authorized user works, a length of employment time, and employment history, location data associated with the authorized user within the facility, etc. Similar to the automated storage and retrieval location data, it should be understood that the administration data and/or the authorized user data may correspond to multiple administrations of monitored units and/or multiple associated authorized users (e.g., of the particular associated facility).

The computer system may be then aggregate and collate the data (e.g., similar to as described in reference to FIG. 11) to be used in training the prediction model. For example, the computer system may compute feature vectors 1408 to generate training samples based on the data received from the various data sources. The computed feature vectors 1410 may include a plurality of features. For example, in some embodiments, the plurality of features may correspond to those listed in Table 1, above. In some embodiments, the plurality of features may include any suitable type and/or number of features. For example, as described herein, a feature may be computed (e.g., derived) from raw data obtained from one or more sources. For example, a feature may be a percentile statistic that relates one user to another user. In another example, a feature may be a percentage value (e.g., percentage of dispenses of a controlled monitored unit over a given time period), an average value over a given time period (e.g., average number of pain reassessments missing), etc. In some embodiments a feature (e.g., feature "F1," feature "F2," etc., as depicted in diagram 1400) may correspond to an alphanumeric value which may be used as input to a machine learning model. In some embodiments, a feature from a training sample may be used to adjust one or more weights of the machine learning model (e.g., the prediction model). These one or more weights may subsequently be used to output a prediction by the trained model (e.g., via an ensemble model of multiple decision trees). In some embodiments, multiple feature vectors 1410 may be determined, for example, per training sample.

In some embodiments, the computer system may also determine ground truth labels 1412 associated with one or more (e.g., all) of the training samples. For example, one or more ground truth labels 1414 (e.g., label "L1," label "L2," etc.) may, respectively, correspond to the feature vectors 1410. The ground truth label may indicate whether or not a particular sample is associated with a user who is a known diverter (e.g., a user who is known to be associated with one or more anomaly events). The ground truth labels may be used to train the prediction model.

As described in reference to FIGS. 9 and 10, the computer system may determine to process (e.g., curate) the training data to ensure more the prediction model is more accurately trained. For example, in some embodiments, the real world data may correspond to a situation in which only a small percentage (e.g., 5%) of users are true diverters, while the remaining super-majority are non-diverters (e.g., not associated with any anomaly events). Accordingly, without further curation of training data samples, the training data set may be imbalanced. Upon determining the ground truth labels 1412 and/or computing the feature vectors 1408 for training data, the computer system may determine whether the diverter and non-diverter training sample sets are balanced 1416. For example, the computer system may determine if a difference between the number of diverters in the training sample data set is the number of non-diverters in the training sample data set is within a predefined threshold difference (e.g., 1%, 5%, 10%, etc.). If yes, the computer system may proceed to train the prediction model 1422. If no, the computer system may down-sample the training data set(s) 1418. For example, the computer system may select (e.g., accordingly to any suitable algorithm and/or selection process) a subset of non-diverter training samples so that a difference between the number of data samples of the subset of non-diverter samples and the number of data samples of the diverter set is within a predetermined differential value.

In some embodiments, the computer system may determine a plurality of training data sets to be used for training the prediction model 1422. In some embodiments, the computer system may also determine one or more validation sets (e.g., holdout sets) with a real-world percentage of diverter samples 1420. These validation sets may approximate the true rate of diversion in the real world, and may be used to validate the trained model 1426 subsequent to the training the prediction model 1422. In some embodiments, the training process may be similar to as described in reference to FIGS. 9 and 10. For example, the computer system may determine model parameters 1424 for training the model. In one example, whereby the prediction model is an ensemble of decision trees, the parameters may include a number of trees (e.g., 50), a maximum depth (e.g., 5), etc. In some embodiments, the parameters may be chosen based at least in part on a grid search that is used to optimize performance.

Figure 15:
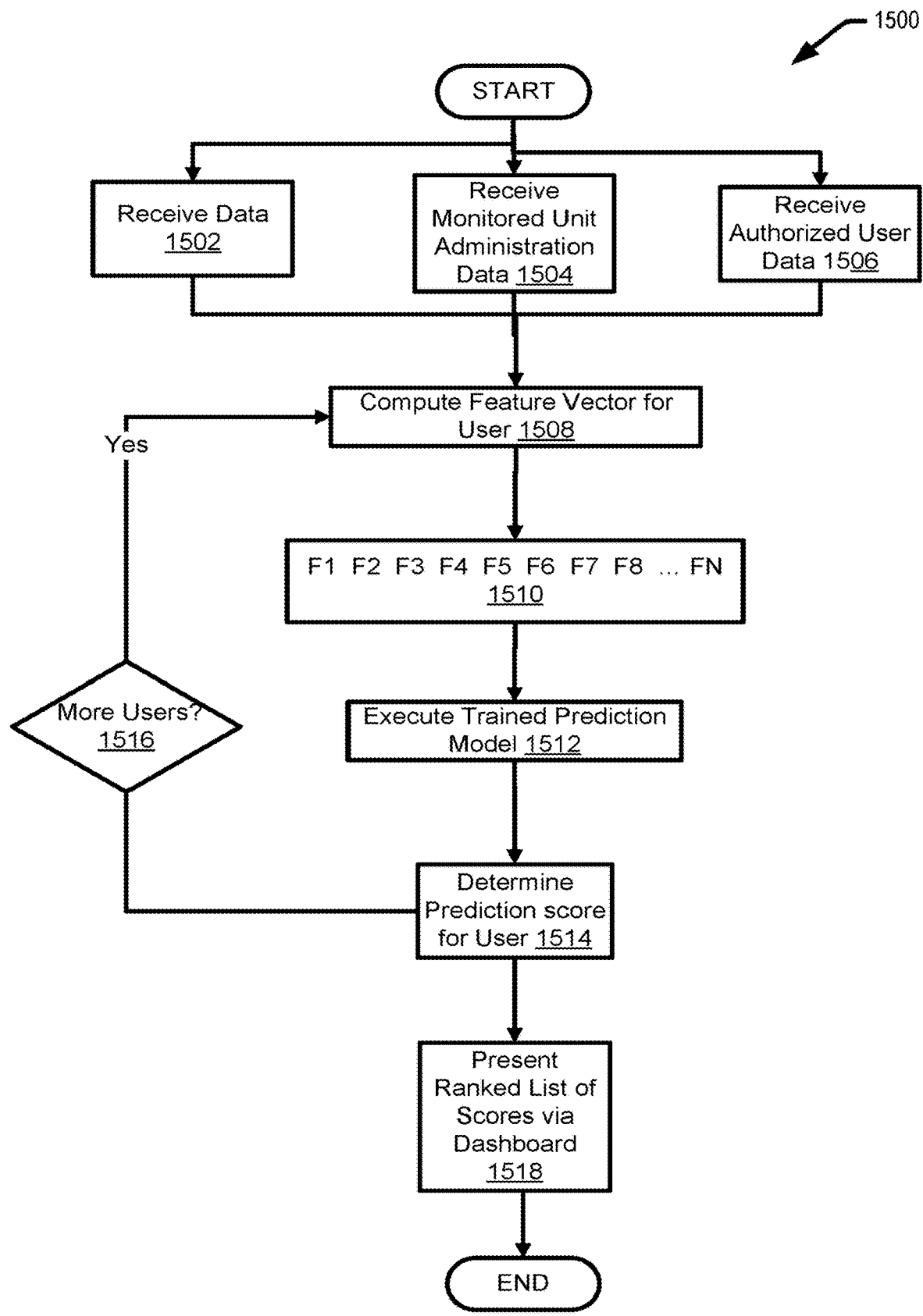
FIG. 15 is an example flow diagram illustrating a flow for executing a trained prediction model to generate a prediction that a user is associated with one or more anomaly events, according to at least one example.

FIG. 15 is an example flow diagram illustrating a flow for executing a trained prediction model to generate a prediction that a user is associated with one or more anomaly events, according to at least one example. In flow 1500, a computer system may execute the trained prediction model that was trained, for example, according to the process described in reference to FIG. 14.

Flow 1500 of FIG. 15 begins with the computer system receiving data from one or more data sources. For example, the computer system may receive automated storage and retrieval location data 1502, receive monitored unit administration data 1504, and receive authorized user data 1506. In some embodiment, these steps may be similar to as described in reference to flow 1400. In this case, the received data may be receive on any suitable cadence (e.g., once a day). The received data may be collected over a period of time (e.g., six months, a year, etc.) so that historical data may be collected. In some embodiments, the received data may be associated with any suitable number and/or type of users (e.g., dependent users, authorized users) of one or more facilities, any suitable number and/or type of monitored units (and/or respective automated storage and retrieval locations throughout the facility), and or any suitable number of usage data. As described herein, the received data may be associated with one or more data attributes.

The computer system may then compute a feature vector for a particular user 1508 to generate the feature vector 1510. In some embodiments, the feature vector 1510 may include similar (e.g., the same) features that were used to train the prediction model of the system. In some embodiments, the feature vector may be generated based in part on the one or more data attributes. In some embodiments, as described herein, the features may include statistical data. The statistical data may be generated based in part on historical data collected over time. The statistical data may also be generated relative to other users (e.g., including percentile ranking information). In some embodiments, by defining at least a portion of the features relative to other users (e.g., of a common role type within the same facility), embodiments may enable more accurate comparisons between users. For example, the environmental conditions of one facility may be quite different from the conditions of another facility. For example, there may be a limited amount of computing and/or human resources in one facility. Also, some facilities may have different procedures. This may impact some of the data collection (e.g., a time between administration of the monitored unit versus when it was logged, an amount of dosage wasted, etc.).

In some embodiments, the feature vector 1510 may be input into the trained prediction model and the computer system may execute the trained prediction model 1512. The system may then determine a prediction score for the particular user 1514. The prediction score may indicate a level of risk that the user (e.g., an authorized user) is associated with at least one anomaly event (e.g., that the user has diverted a monitored unit one or more times). As described herein, the score may be suitable for ranking the user along with other users (e.g., of the same facility and/or having a common role type).

The system may determine if there are any more users 1516 (e.g., of a department, facility, campus, etc.) to compute prediction scores for. If so, the system may repeat the process of generating a feature vector (e.g., for another authorized user) and utilizing the features to execute the trained prediction model 1512. Eventually, the system may present a list of prediction scores via a dashboard (e.g., similar to dashboard 1300 of FIG. 13) on a user device. The dashboard may be operable for triaging and remediating issues related to potential anomaly events and/or potential diverters.

Figure 16:
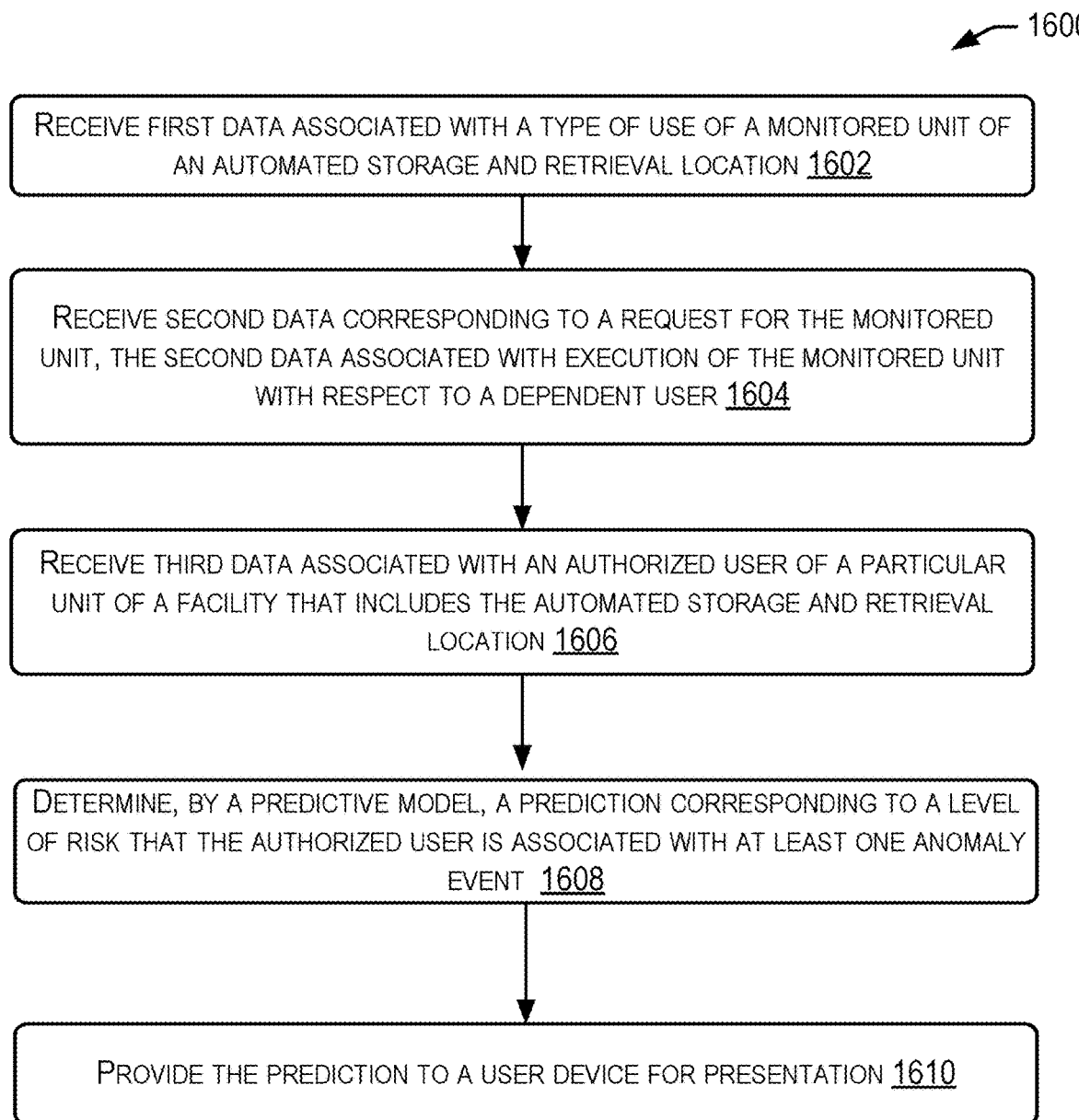
FIG. 16 is an example flow diagram illustrating a process for a prediction system providing a prediction for efficiently identifying and/or remediating anomaly events, according to at least one example.

FIG. 16 is an example flow diagram illustrating a process for a prediction system providing a prediction for efficiently identifying and/or remediating anomaly events, according to at least one example. The process 1600 and any other processes described herein, are illustrated as logical flow diagrams, each operation of which represents a sequence of operations that can be implemented in hardware, computer instructions, or a combination thereof. In the context of computer instructions, the operations may represent computer-executable instructions stored on one or more non-transitory computer-readable storage media that, when executed by one or more processors, perform the recited operations. Generally, computer-executable instructions include routines, programs, objects, components, data structures and the like that perform particular functions or implement particular data types. The order in which the operations are described is not intended to be construed as a limitation, and any number of the described operations can be combined in any order and/or in parallel to implement the processes.

Additionally, some, any, or all of the processes described herein may be performed under the control of one or more computer systems configured with specific executable instructions and may be implemented as code (e.g., executable instructions, one or more computer programs, or one or more applications) executing collectively on one or more processors, by hardware, or combinations thereof. As noted above, the code may be stored on a non-transitory computer readable storage medium, for example, in the form of a computer program including a plurality of instructions executable by one or more processors.

At block 1602 of process 1600, a computer system receives first data associated with a type of use of a monitored unit (e.g., a monitored controlled unit) of an automated storage and retrieval location (e.g., a computer-controlled drug storage cabinet). The computer system may be similar to any of the computer systems described herein, operable for training and/or executing a prediction model to generate a prediction score. The first data may include a plurality of first data attributes associated with the monitored controlled unit of the automated storage and retrieval location. The automated storage and retrieval location may store one or more monitored controlled units. The type of use of the monitored controlled unit may include at least one of (I) administration of the monitored controlled unit to a user (e.g., a dependent user, such as a patient), (II) discarding of the monitored controlled unit, or (III) returning the monitored controlled unit to the automated storage and retrieval location. It should be understood that there may be other types of usage also determined based in part on the first data (e.g., a transfer of the monitored unit from the automated storage and retrieval location to another automated storage and retrieval location of the same facility). It should be understood that the computer system may receive within the first data information about the usage of multiple monitored units, for example, over a period of time. In some embodiments, the first data may be received from a first data source, which may be the automated storage and retrieval location and/or a computer connected to the automated storage and retrieval location.

At block 1604, the computer system may receive second data corresponding to an order for the monitored controlled unit. The order may be associated with an electronic record of the dependent user, and the second data may be associated with an administration of the monitored controlled unit to the dependent user. In some embodiments, the second data may include a plurality of second data attributes that identify one or more of a dosage associated with the order, a frequency associated with the order, a scale associated with the order, an identity of an authorized user associated with the order, an identity of the dependent user, a time at which the monitored controlled unit was administered to the dependent user, or a quantity of the monitored controlled unit administered to the dependent user. In some embodiments, the plurality of second data attributes identify an admission time associated with the dependent user, a discharge time associated with the dependent user, one or more tests performed on the dependent user, or results from one or more pain assessments performed on the dependent user. In some embodiments, the second data may include information about a plurality of orders. In some embodiments, the second data may be received from a second data source, such as an electronic data warehouse.

At block 1606, the computer system may receive third data associated with an authorized user of a particular unit of a facility that includes the automated storage and retrieval location. In some embodiments, the authorized user may be one of a plurality of authorized users of the facility that includes the automated storage and retrieval location. In some embodiments, the third data may include information about where the authorized user (and/or other authorized users) were located at a first time when the monitored controlled unit was removed from the automated storage and retrieval location. In some embodiments, the third data may be received from a third data source, which may include an electronic data warehouse, a scheduling application, a timekeeping application, or a geolocation system. In some embodiments, the computer system may receive, within the third data, information about the plurality of other authorized users. This may enable the computer system to determine a percentile score of the authorized user that relates the authorized user to other authorized users of the plurality of authorized users of the facility. In some embodiments, the percentile score may be computed relative to other users of the same facility (and/or unit within the facility) having a common role type (e.g., common job description).

At block 1608, the computer system may determine a prediction corresponding to a level of risk that the authorized user is associated with at least one anomaly event. In some embodiments, the prediction may be determined based at least in part on at least one of the first data, the second data, or the third data (e.g., as described in reference to FIG. 15). In some embodiments, the level of risk may correspond to a particular pattern of behavior indicative of at least one anomaly event. In some embodiments, the prediction model may determine the level of risk based at least in part on the type of use involving the monitored controlled unit. In some embodiments, the prediction model is trained based at least in part on features derived from at least one of the first data attributes, the second data attributes, or the third data attributes, for example, as described in reference to FIG. 14. In some embodiments, the training may be based at least in part on one or more percentile scores associated with the respective authorized user. The percentile score may be associated with the type of use involving one or more monitored controlled units. In some embodiments, the prediction model is trained based at least in part on a plurality of features, A feature of the plurality of features may be associated with at least one of: (I) a pattern of use by an authorized user involving one or more monitored controlled units, (II) a score associated with a condition of a dependent user before or after being administered a monitored controlled unit, or (III) a comparison between the pattern of use by an authorized user and a second pattern of use by another authorized user.

At block 1610, the computer system provides the prediction to a user device for presentation. In some embodiments, the prediction is presented via a graphical user interface (GUI) of the user device that corresponds to a dashboard. In some embodiments, the dashboard is operable for ranking a level of risk of the authorized user in comparison with levels of risk of other authorized users of the facility (e.g., see FIG. 13). In some embodiments, the dashboard may provide recommendations for specific remediation steps to take with respect to the authorized user associated with the prediction. In some embodiments, the dashboard may highlight specific factors for why the authorized user may be indicated as being recommended to receive remediation action (e.g., a number of wastes, a number of monitored unit variances, discrepancies in pain reassessment scores, etc.).

Specific details are given in the above description to provide a thorough understanding of the examples. However, it is understood that the examples may be practiced without these specific details. For example, circuits may be shown in block diagrams in order not to obscure the examples in unnecessary detail. In other instances, well-known circuits, processes, algorithms, structures, and techniques may be shown without unnecessary detail in order to avoid obscuring the examples.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the examples may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, examples may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A computer-implemented method, comprising:
receiving, by a computer system from one or more data sources, first data comprising a plurality of first data attributes associated with a monitored controlled unit of an automated storage and retrieval location, the automated storage and retrieval location comprising a storage unit in which is retained monitored controlled units, and the first data associated with a type of use involving the monitored controlled unit;
receiving, by the computer system from the one or more data sources, second data comprising a plurality of second data attributes corresponding to a request for the monitored controlled unit of the monitored controlled units retained in the automated storage and retrieval location, the request associated with an electronic record of a dependent user, and the second data associated with an order for the monitored controlled unit with respect to the dependent user;
receiving, by the computer system from the one or more data sources, third data comprising a plurality of third data attributes associated with an authorized user of a location that includes the automated storage and retrieval location;
determining, by a prediction model of the computer system, a prediction indicative of the authorized user being associated with at least one anomaly event, the prediction determined based at least in part on at least one of the first data, the second data, or the third data, and wherein the prediction model is trained based at least in part on features derived from at least one of the first data attributes, the second data attributes, or the third data attributes; and
providing, by the computer system, the prediction to a user device for presentation.

2. The computer-implemented method of claim 1, wherein the authorized user is one of a plurality of authorized users of the location having a common role type, and wherein the method further comprises:
determining, by the computer system, a percentile score of the authorized user that relates the authorized user to other authorized users of the plurality of authorized users of the location having the common role type; and
training, by the computer system, the prediction model based at least in part on the percentile score.

3. The computer-implemented method of claim 2, wherein the percentile score is associated with the type of use involving one or more monitored controlled units, the type of use including at least one of: (I) administration of the monitored controlled unit to the dependent user, (II) discarding of the monitored controlled unit, or (III) returning of the monitored controlled unit to the automated storage and retrieval location.

4. The computer-implemented method of claim 1, wherein the prediction is presented via a graphical user interface of the user device that corresponds to a dashboard, the dashboard operable for ranking a level of the authorized user in comparison with levels of other authorized users of the location.

5. The computer-implemented method of claim 1, wherein the prediction corresponds to a particular pattern of behavior indicative of the at least one anomaly event, the prediction model determining prediction based at least in part on the type of use involving the monitored controlled unit.

6. The computer-implemented method of claim 1, further comprising:
receiving, by the computer system, a first number of data samples that are respectively determined to be associated with non-anomaly events;
receiving, by the computer system, a second number of data samples that are respectively determined to be associated with anomaly events, wherein the first number is greater than the second number;
selecting, by the computer system, a subset of the first number of data samples so that a difference between a third number of data samples of the subset and the second number of data samples is within a predetermined difference; and
training, by the computer system, the prediction model based at least in part on the subset of the first number of data samples and the second number of data samples.

7. The computer-implemented method of claim 1, wherein the prediction model is trained based at least in part on a plurality of features, a feature of the plurality of features associated with at least one of: (I) a pattern of use by an authorized user involving one or more monitored controlled units, (II) a score associated with a condition of a dependent user before or after execution of a monitored controlled unit, or (III) a comparison between the pattern of use by an authorized user and a second pattern of use by another authorized user.

8. The computer-implemented method of claim 1, wherein the plurality of first data attributes identify one or more of an identity of the dependent user, a quantity of the monitored controlled unit removed from the automated storage and retrieval location, a time at which the monitored controlled unit was removed from the automated storage and retrieval location, an identity of a user who removed the monitored controlled unit from the automated storage and retrieval location, or an identification of a use of the monitored controlled unit after removal.

9. The computer-implemented method of claim 1, wherein the plurality of second data attributes identify one or more of a dosage associated with the request, a frequency associated with the request, a scale associated with the order, an identity of an authorized user associated with the request, an identity of the dependent user, a time at which the monitored controlled unit was administered to the dependent user, or a quantity of the monitored controlled unit administered to the dependent user.

10. The computer-implemented method of claim 1, wherein the plurality of second data attributes identify an admission time associated with the dependent user, a discharge time associated with the dependent user, one or more tests performed on the dependent user, or results from one or more pain assessments performed on the dependent user.

11. One or more non-transitory computer-readable storage devices comprising computer-executable instructions that, when executed by one or more computer systems, cause the one or more computer systems to perform operations comprising:
receiving, from one or more data sources, first data comprising a plurality of first data attributes associated with a monitored controlled unit of an automated storage and retrieval location, the automated storage and retrieval location comprising a storage unit in which is retained monitored controlled units, and the first data associated with a type of use involving the monitored controlled unit;
receiving, from the one or more data sources, second data comprising a plurality of second data attributes corresponding to a request for the monitored controlled unit of the monitored controlled units retained in the automated storage and retrieval location, the request associated with an electronic record of a dependent user, and the second data associated with an order for the monitored controlled unit with respect to the dependent user;

receiving, from the one or more data sources, third data comprising a plurality of third data attributes associated with an authorized user of a location that includes the automated storage and retrieval location;

determining, by a prediction model, a prediction indicative of the authorized user being associated with at least one anomaly event, the prediction determined based at least in part on at least one of the first data, the second data, or the third data, and wherein the prediction model is trained based at least in part on features derived from at least one of the first data attributes, the second data attributes, or the third data attributes; and providing the prediction to a user device for presentation.

12. The one or more non-transitory computer-readable storage devices of claim 11, wherein the authorized user is one of a plurality of authorized users of the location having a common role type, and wherein the instructions further comprise performing operations comprising:

determining a percentile score of the authorized user that relates the authorized user to other authorized users of the plurality of authorized users of the location having the common role type; and training the prediction model based at least in part on the percentile score.

13. The one or more non-transitory computer-readable storage devices of claim 11, wherein receiving the first data comprises at least one of: (I) accessing the first data from an archive file generated by the automated storage and retrieval location, or (II) receiving a data stream from the automated storage and retrieval location that includes the first data.

14. The one or more non-transitory computer-readable storage devices of claim 11, wherein the second data is received from an electronic data warehouse configured to retain the electronic record of the dependent user and electronic records of other users.

15. The one or more non-transitory computer-readable storage devices of claim 11, wherein the prediction model is trained based at least in part on a plurality of features, a feature of the plurality of features associated with at least one of: (I) a pattern of use by an authorized user involving one or more monitored controlled units, (II) a score associated with a condition of a dependent user before or after execution of a monitored controlled unit, or (III) a comparison between the pattern of use by an authorized user and a second pattern of use by another authorized user.

16. A system, comprising:
a memory configured to store computer-executable instructions; and
one or more processors configured to access the memory and execute the computer-executable instructions to at least:

receive, from one or more data sources, first data comprising a plurality of first data attributes associated with a monitored controlled unit of an automated storage and retrieval location, the automated storage and retrieval location comprising a storage unit in which is retained monitored controlled units, and the first data associated with a type of use involving the monitored controlled unit;

receive, from one or more data sources, second data comprising a plurality of second data attributes corresponding to a request for the monitored controlled unit of the monitored controlled units retained in the automated storage and retrieval location, the request associated with an electronic record of a dependent user, and the second data associated with an order for the monitored controlled unit with respect to the dependent user;

receive, from one or more data sources, third data comprising a plurality of third data attributes associated with an authorized user of a location that includes the automated storage and retrieval location;

determine, by a prediction model, a prediction indicative of the authorized user being associated with at least one anomaly event, the prediction determined based at least in part on at least one of the first data, the second data, or the third data, and wherein the prediction model is trained based at least in part on features derived from at least one of the first data attributes, the second data attributes, or the third data attributes; and provide the prediction to a user device for presentation.

17. The system of claim 16, wherein the automated storage and retrieval location is a computer-controlled controlled storage and retrieval location.

18. The system of claim 16, wherein the authorized user was located at the location including the automated storage and retrieval location at a first time when the monitored controlled unit was removed from the automated storage and retrieval location, and wherein the one or more data sources includes at least one of a resource application, a record application, or a location system.

19. The system of claim 16, wherein the plurality of first data attributes are further associated with a plurality of automated storage and retrieval locations, and wherein the plurality of second data attributes further correspond to a plurality of requests for a plurality of monitored controlled units.

20. The system of claim 16, wherein the prediction is presented via a graphical user interface of the user device that corresponds to a dashboard, the dashboard operable for ranking a level of the authorized user in comparison with levels of other authorized users of the location.

* * * * *